US010227364B2

(12) United States Patent
Wolter et al.

(10) Patent No.: US 10,227,364 B2
(45) Date of Patent: Mar. 12, 2019

(54) SILANE AND SILICIC ACID (HETERO)POLYCONDENSATE HAVING AROMATIC COMPOUNDS LINKED VIA COUPLING GROUPS WHICH ARE SUITABLE AS OR FOR MATRIX SYSTEMS HAVING HIGH TRANSLUCENCY AND GOOD MECHANICAL PROPERTIES

(71) Applicant: Fraunhofer-Gesellschaft zur Foerderung der angewandten Forschung e.V., Munich (DE)

(72) Inventors: Herbert Wolter, Tauberbischofsheim (DE); Somchith Nique, Eisingen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 83 days.

(21) Appl. No.: 14/910,487

(22) PCT Filed: Aug. 7, 2014

(86) PCT No.: PCT/EP2014/067015
§ 371 (c)(1),
(2) Date: Feb. 5, 2016

(87) PCT Pub. No.: WO2015/018906
PCT Pub. Date: Feb. 12, 2015

(65) Prior Publication Data
US 2016/0185804 A1 Jun. 30, 2016

(30) Foreign Application Priority Data
Aug. 8, 2013 (DE) .................. 10 2013 108 594

(51) Int. Cl.
*A61K 6/08* (2006.01)
*C07F 7/18* (2006.01)
(Continued)

(52) U.S. Cl.
CPC .......... *C07F 7/1804* (2013.01); *A61K 6/0091* (2013.01); *A61K 6/093* (2013.01);
(Continued)

(58) Field of Classification Search
CPC ....................................................... A61K 6/08
See application file for complete search history.

(56) References Cited

U.S. PATENT DOCUMENTS 5,233,006 A 8/1993 Wolter et al.
5,399,738 A 3/1995 Wolter et al.
(Continued)

FOREIGN PATENT DOCUMENTS

DE 4011044 A1 10/1991
DE 4416857 C1 6/1995
(Continued)

OTHER PUBLICATIONS

Burke et al., "Synthesis of Ethisolide, Isoavenaciolide, and Avenaciolide," J. Org. Chem., vol. 57, No. 8, p. 2228-2235 (1992).
(Continued)

*Primary Examiner* — Michael F Pepitone
(74) *Attorney, Agent, or Firm* — Duane Morris LLP

(57) ABSTRACT

The present invention relates to compounds and silicic acid (hetero)polycondensates comprising structures of formulas (1) and/or (2),

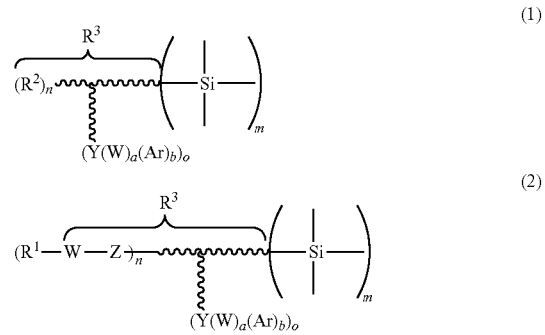

$R^2$ is a hydroxy group or a free carboxylic acid residue or a carboxylic acid ester derived therefrom or a salt derived therefrom, $R^3$ denotes a residue having a hydrocarbon-containing branched or unbranched backbone which is bonded to silicon by carbon, and can be arbitrarily interrupted by heteroatoms or coupling groups or by other heteroatom-containing groups, where the zigzag line purely schematically denotes the hydrocarbon-containing backbone, the three not more closely characterized bonds of the Si-atom represent additional residues bonded to the silicon atom, selected from residues that can be hydrolyzed from silicon, hydroxy groups and residues bonded to silicon by carbon which can have the same meaning as $R^3$ or can have a different meaning deviating therefrom, or represent oxygen bridges to further silicon atoms and/or other metal atoms in the case the structure (1) is part of a silicic acid (hetero)polycondensate, the residue Y is either divalent, and then has the meaning of —S—, —NR$^4$— or —P(O)(R$^4$)$_c$(Z')$_d$— with Z'=OR$^4$, c=0 or 1, d=0 or 1 and (c+d)=1, or trivalent and has the meaning of —N= or —P(O)=, $R^4$ represents a hydrocarbon-containing residue and in the —NR$^4$— residue can in addition have the meaning of hydrogen, (Continued)

W is a substituted or unsubstituted hydrocarbon residue bonded to Y, the chain of which can be interrupted by —S—, —O—, —NH—, —NR$^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, Ar is a residue that carries at least one aromatic group which is unsubstituted or substituted with one or more residues, where the aromatic groups do not carry substituents, selected from boronic acid-, the carboxylic acid-, the phosphine acid-, the phosphonic acid- and the sulfonic acid group and from hydroxy groups, where Ar must be bonded to W if a≠0, Z is selected from urethane-, acid amide-, ether- and ester groups, R$^1$ is a straight chain or branched, organically polymerizable group carrying at least one C=C double bond, and the index e is 1, 2, 3, 4 or an integer greater than 4, the index a is equal to 0 or 1 or 2, the index b=1, 2, 3 or an integer greater than 3 if a≠0, and b=1 or 2 if a=1, the index m is 1, 2 or an integer greater than 2, the index n is 0, 1, 2 or greater than 2 and the index o is 1 or 2 or greater than 2.

composites and organically polymerized masses produced therefrom and methods for producing the same.

22 Claims, No Drawings

(51) Int. Cl.
| | |
|---|---|
| C07F 7/08 | (2006.01) |
| A61K 6/00 | (2006.01) |
| A61K 6/093 | (2006.01) |
| C07F 9/53 | (2006.01) |
| C08G 77/00 | (2006.01) |
| C08G 79/04 | (2006.01) |

(52) U.S. Cl.
CPC ............ *C07F 7/081* (2013.01); *C07F 7/1892* (2013.01); *C07F 9/5325* (2013.01); *C08G 77/80* (2013.01); *C08G 79/04* (2013.01)

(56) References Cited

U.S. PATENT DOCUMENTS

| | | |
|---|---|---|
| 5,532,398 A | 7/1996 | Wolter et al. |
| 5,717,125 A | 2/1998 | Wolter et al. |
| 5,792,881 A | 8/1998 | Wolter et al. |
| 6,106,606 A | 8/2000 | Gellermann et al. |
| 6,124,491 A | 9/2000 | Wolter et al. |
| 6,447,907 B1 | 9/2002 | Wolter et al. |
| 6,794,527 B1 | 9/2004 | Wolter et al. |
| 2007/0135572 A1 | 6/2007 | Wolter |
| 2008/0187499 A1 | 8/2008 | Wolter et al. |
| 2008/0319127 A1 | 12/2008 | Wolter |
| 2009/0023883 A1 | 1/2009 | Wolter |
| 2011/0082250 A1 | 4/2011 | Wolter |
| 2014/0221521 A1 | 8/2014 | Wolter et al. |
| 2014/0249325 A1 | 9/2014 | Wolter et al. |
| 2015/0274862 A1 | 10/2015 | Wolter et al. |

FOREIGN PATENT DOCUMENTS

| | | |
|---|---|---|
| DE | 19627198 A1 | 1/1997 |
| DE | 19643781 A1 | 4/1998 |
| DE | 19832965 A1 | 2/2000 |
| DE | 19910895 A1 | 9/2000 |
| DE | 10018405 A1 | 10/2001 |
| DE | 10041038 B4 | 3/2002 |
| DE | 10132654 A1 | 10/2002 |
| DE | 10349766 A1 | 6/2005 |
| DE | 102005018059 A1 | 10/2006 |
| DE | 102005018351 A1 | 11/2006 |
| DE | 102005061965 A1 | 7/2007 |
| DE | 102011053865 A1 | 3/2013 |
| DE | 102011054440 A1 | 4/2013 |
| DE | 102012109685 A1 | 4/2014 |
| EP | 0450624 A2 | 10/1991 |
| WO | WO2013/041723 A1 | 3/2013 |
| WO | WO2013/053693 A1 | 4/2013 |

OTHER PUBLICATIONS

Kato et al., "Large Photoinduced Refractive Index Change of Polymer Films Containing and Bearing Norbornadiene Groups . . . ," Polymer Journal, vol. 33, No. 11, p. 868-873 (2001).

SILANE AND SILICIC ACID (HETERO)POLYCONDENSATE HAVING AROMATIC COMPOUNDS LINKED VIA COUPLING GROUPS WHICH ARE SUITABLE AS OR FOR MATRIX SYSTEMS HAVING HIGH TRANSLUCENCY AND GOOD MECHANICAL PROPERTIES

The present invention relates to inorganic-organic materials, namely silanes, resins and matrix systems (organically cross-linked or non-cross-linked silicic acid (hetero)polycondensates provided with fillers, if required) having aromatic residues linked thereto via coupling groups, the (molar) amount of which can be precisely adjusted. The named aromatic groups and their (molar) amount effect the refractive index of the cured resins or of the inorganic-organic materials produced from the resins by organic polymerization. By appropriate selection of the substituents and the amount in which they are incorporated into the silicic acid (hetero)polycondensates, the refractive index of the material can be precisely controlled, and thereby an adjustment of the refractive index of the material to the refractive index of fillers with which it is to be filled attained. By adjustment of a specific refractive index difference between the material and the filler, a specific translucency or optionally also a specific turbidity can be obtained as desired, while, as a rule, an identical or almost identical refractive index of the matrix material and the filler embedded therein leads to particularly high translucency. A material filled in such a way can therefore be utilized in various fields in a particularly advantageous manner. This includes the dental field in which specially required aesthetics can be realized by tuning the desired translucency, while the possibility of controlling radio-opacity enables use e.g. for optical applications without the achievement of the desired respective mechanical properties, for example, a specific elastic modulus, thereby being adversely affected. A particular advantage of the systems is that resins and matrix systems can be generated which can be tuned continuously or with a very fine graduation with respect to the refractive index or translucency, so that the user can resort to a large number of material/filler combinations from which the respectively desired material can be precisely selected.

In the field of dental materials, but not only there, it is important to be able to provide a variety of materials, which can be principally used for the same purposes and have the same physical and mechanical properties, whereby, however, these properties must be finely tuned to specific, often even individual, requirements. Examples are the color or translucency of crowns, the matrix hydrophilicity, the shrinkage, the reactivity to substrates or other matrix- or composite components, such as dental tissue, co-reactants or reaction partners in ionomer compositions where the smallest changes often have a large effect. If the specialist working with these materials, for example a dentist or a dental technician, can resort to a graduated range of materials required for his purposes, he is enabled to select the material that is an exact match for each individual application.

The production of a highly aesthetic dental prosthesis was already proposed in DE10 2011 054440.2. Some of the materials disclosed there, however, are not commercially available or are relatively expensive to manufacture. There is therefore a need to provide additional materials that do not require the use of the substituents and fillers employed there and that can be produced in a relatively simple and cost-effective manner with high variability.

The solution to the named problem is the provision of the inventive organically modified silicic acid polycondensates and composites produced therefrom having a certain, controllable amount of an aromatic group, which is bonded via nitrogen, sulfur or phosphorus to a hydrocarbon residue bonded to silicon via carbon. The invention also provides silanes as starting materials for said silicic acid polycondensates. In specific embodiments of the invention, the silicic acid polycondensates further contain free hydroxy- or carboxylic acid groups and/or C═C double bond-containing residues that are accessible to organic polymerization (polyaddition) or can be bridged to each other by further reactions, or they contain dimeric or oligomeric silane structures. All of these groups, residues and structures allow further fine graduations with respect to reactivity and/or strength of the condensates and composites, as explained in the following in detail.

The organically modified silicic acid polycondensates according to the invention can be silicic acid polycondensates composed exclusively of silanes or they can be co-condensed compounds containing, in addition to silicon, metal atoms M, for example, M═B, Al, Ti, Zn and/or other transition metal atoms, such as known in principle from the state of the art. Condensates containing such heteroatoms are referred to in the present invention as silicic acid hetero polycondensates, and the collective possible condensates with and without heteroatoms as silicic acid (hetero)polycondensates. The condensates can further be completely or partially cross-linked condensates of silanes and optionally metal compounds, in particular metal alkoxide compounds. If the condensates are only partially cross-linked, they further exhibit hydrolytically condensable residues or free hydroxy groups bonded to silicon and/or metal, which allow (subsequent) further inorganic cross-linking with formation of additional Si—O—Si or Si—O-M or M-O-M-bridges. If the term "silicic acid polycondensate" is used, the term according to the application includes both hetero—as well as partial condensates, unless excluded based on the context.

The silanes according to the invention have the following formula (1). The silicic acid polycondensates according to the invention have structures of the following formula (1):

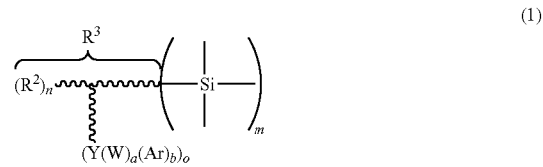

In this formula, the zigzag line denotes the backbone of a hydrocarbon residue (substituent), which is bonded via a carbon atom to the silicon where this backbone can be arbitrarily interrupted by heteroatoms or coupling groups or by other heteroatom-containing groups. Examples are interruptions by —S—, —O—, —NH, —C(O)O—, —NHCH(O)—, —C(O)NH—, —NHC(O)O—, —C(O)NHC(O)—, —NHC(O)NH—, —S(O)—, —C(S)O—, —C(S)NH—, —NHC(S)—, —NHC(S)O— and the like. Since for the purposes of the invention the structure of the backbone of this residue is not relevant, those of skill in the art may make an arbitrary selection. The depicted branching of the hydrocarbon-containing backbone, shown by the branched zigzag line, is also optional, as well as the possibility of a multiple branching. The position of the $R^2$ and $Ar(W)_aY$ residues on the backbone is also freely selectable.

This entire substituent or residue, which is bonded to the silicon atom via a carbon atom, is referred to as $R^3$ in formula (1). It is o-fold substituted with $(Ar)_b(W)_aY$— where Ar has the meaning of a group that contains at least one aromatic residue containing at least one aryl- and/or heteroaryl group. The aryl- and heteroaryl groups can be unsubstituted; they can also be mono- or polysubstituted instead, where the substituents are preferably selected from alkyl, alkoxy, alkylmercapto, alkoxy alkylene, alkoxy thio-alkylene, alkoxy carbonyl, alkyl ketoalkylene (also to be referred to as alkyl carbonylalkylene), alkyl carboxyl, alkyl carboxylalkylene, nitrile and halogen (in particular chlorine, bromine, iodine). In contrast, substitution with acid groups (e.g. boronic acid-, carboxylic acid-, phosphine- or phosphonic acid- or sulphonic acid groups) or hydroxy groups is less desirable and should be avoided if at all possible. If the aromatic residue contains several aryl groups, they can be interrupted by other groups, preferably selected from —$R^x$—, —$(R^x)_x$—C(O)—$(R^y)_y$—, —$(R^x)$—, —S—$(R^y)_y$—, —$(R^x)_x$—S(O)—$(R^y)_y$—, —$(R^x)_x$—S(O)$_2$—$(R^y)_y$—, —$(R^x)_x$—O—$(R^y)_y$— and —$(R^x)_x$—C(O)$_2$—$(R^y)_y$—, where $R^x$ and $R^y$ can be identical or different and preferably have the meaning of a short-chain alkylene group (e.g. with $C_1$-$C_6$, including —CH$_2$— and —C(CH$_3$)$_2$—), and the indices x and y have the meaning of 0 or 1 independently of one another. In many cases, both x and y thereby have the meaning of 0. Bisphenol-A-, benzophenone-, diphenyl sulfone-, diphenyl sulfide- or diphenyl ether structures are examples thereof. Alternatively, the existing aryl groups can be linked to each other by a bond (such as e.g. in the biphenyl-, terphenyl- or bipyridyl residue) or be present in condensed form (such as e.g. in the naphtyl-, anthracene-, chrysene residue).

The aforementioned examples related to aromatics without heteroatoms in the ring. The following are to be named as exemplary heteroaryl groups: thiophene-, furan-, pyridine, and the quinoline structure.

The index o has the meaning of 1, 2, 3 or 4, but can optionally also be even greater. Preferably, o=1 or 2, most preferably 1. The index a is 0, 1 or 2. This means that the W group can be present once or twice or can be absent. W is a substituted or unsubstituted hydrocarbon group, for example, an alkylene or an alkenylene group the carbon chain of which many be interrupted by arbitrary heteroatoms or coupling groups, such as —S—, —O—, —NH—, —$NR^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—.

The Y residue is either divalent, and then has the meaning of —S—, —$NR^4$— or —$P(O)(R^4)_c(Z')_d$— with $Z'$=$OR^4$, c=0 or 1, d=0 or 1 and (c+d)=1, or it is trivalent and has the meaning of —N= or -p(O)=.

In the case the W group is absent, the one or several Ar residue(s) are directly bonded to Y. Depending on whether Y is divalent or trivalent, one or two Ar residue(s) can thereby be bonded to Y. In these cases, b must therefore be 1 or 2. In the presence of W, b can also be 1 or 2, but can also be greater, for example, 3, 4, 5, or 6 or even represent an even higher number. At least one Ar residue must thereby be bonded to each W group; however, several (two or even more) residues per W group are also possible.

In all of the above contexts, $R^4$ represents a substituted or unsubstituted hydrocarbon residue, for example, an aryl-, alkylaryl- or arylalkyl residue and preferably a substituted or—preferably—unsubstituted alkyl residue, more preferably having 1 to 6 carbon atoms. Except in the formula —$P(O)(R^4)_c(Z')_d$—, $R^4$ can in addition also have the meaning of hydrogen in all of these contexts (the exception also applies to the definition $Z'$=$OR^4$; here, too, $R^4$ cannot have the meaning of hydrogen).

The $R^3$ substituent or residue can further be substituted with the $R^2$ residue. This residue is a reactive substituent selected from a hydroxy group, a free carboxylic acid residue —COOH or an ester or a salt thereof. This presence of the residue is not necessarily required (n=0), or it can be present once or several times (n=1, 2, 3, 4, or >4). In the case it is present several times, the $R^2$ residues can be identical or also different. Silicic acid polycondensates may also contain different $R^3$ residues of which only some carry one, optionally also several, $R^2$ residues. Several $R^2$ residues on a $R^3$ residue can be located at arbitrary positions on the hydrocarbon skeleton of $R^3$ with the proviso that they are bonded to a carbon atom.

The aforementioned variable options of $R^2$ being present on the $R^3$ substituents or residues substantially contributes in particular to the desired adjustable graduation of the cross-linking degree, where this graduation is independent of the likewise tunable graduation of the refractive index, as described below in more detail.

The $R^3$ substituent or residue can, but is not required to, carry in addition to the shown $R^2$ residue additional, optionally in principle also reactive substituents, which then, however, do not play a role in the present invention.

If (1) is a silane, the three not closer characterized bonds of the Si-atom represent additional silicon atom-bonded residues such as is known from the state of the art. Instead, at least some or all of the bonds can symbolize oxygen bridges to other silicon atoms or other metal atoms if the structure (1) is a component of a silicic acid (hetero) polycondensate. Since the reactions leading to the invention can be conducted on monomeric silanes as well as on already inorganically cross-linked silicic acid polycondensates, the nature of these bonds is not relevant, because in the case of silanes they can subsequently be subjected to hydrolytic condensation and thereby converted into a silicic acid polycondensate.

The first group of the further residues of silane bonded to the silicon atom to be named are residues which are bonded to the silicon atom by carbon. Any residues are suitable for this purpose, including alkyl- (preferably $C_1$-$C_6$-alkyl) and alkenyl residues. These can be substituted or unsubstituted. In specific cases, they are one (and very rarely even two) additional $R^3$ substituent(s) or residue(s) as defined above. The second group to be named are groups that are hydrolyzable under hydrolysis conditions. Those of skill in the art are familiar with these from a large number of publications; therefore, they do not need to be explained in more detail here. In addition to hydrocarbon residues bonded to silicon by an oxygen atom including alkoxides (preferably $C_1$-$C_6$-alkoxy) and acyl residues, they comprise halogen atoms such as Cl or Br, amino groups and the like. In addition to substituents or residues from these two groups, the inventive silanes as well as the inventive silicic acid polycondensates can optionally also carry free OH groups.

In the silanes, the proportion of residues bonded to the silicon atom by carbon to hydrolytically condensable residues or OH is in principle not critical; those of skill in the art know that in the case of three hydrolytically condensable residues or OH groups a very dense inorganic network forms, while in the event two such residues or OH groups are present chains and rings are predominantly formed. In the presence of only one such residue/one OH group only dimers can be formed. Therefore, suitable variants or combinations of these are selected depending on the application; as a rule, precursor silanes having 2 hydrolytically condensable residues or OH groups are well suited for the invention.

The index m is 1 or 2, but optionally also 3, 4 or even greater. Theoretically, there is no upper limit. If m>1, the hydrocarbon-containing $R^3$ residue contains more than one silyl group.

As mentioned above, the index o has the meaning of 1, 2, 3 or 4, but can optionally also be even greater. In the case that o is 2 or greater than 2, the two or more $Y(W)_a(Ar)_b$ residues can have a different meaning in the context of the aforementioned definition. However, it is preferred that o=1. Several $Y(W)_a(Ar)_b$ residues can be bonded to any carbon atom of the structure (1) or of the silane (1).

In the case of silicic acid polycondensates, it is also possible that o=1 or greater than 1 in some of the $R^3$ substituents or residues as specified above, while o=0 in some of the other $R^3$ substituents or residues, hence the $Y(W)_a(Ar)_b$ residue is not present. In these cases, it is preferred that o=1 or greater in at least approximately every fifth $R^3$ residue; hence that o is on average at least 0.2 over the number of $R^3$ substituents or residues. It is more preferred that at least every second $R^3$ residue carries one (or several) $Y(W)_a(Ar)_b$ residues; hence, that o has a value of between 0.5 and 1. The value can, however, also be greater than 1, e.g. 1.5 or 2.0, or even greater. In all of these embodiments, different $R^3$ substituents or residues can also be substituted with different $Y(W)_a(Ar)_b$ residues as specified above in the case that a $R^3$ substituent or residue has more than one such residue; hence that o= or >2. The invention further comprises mixtures of silanes having different $R^3$ substituents or residues, where in the different $R^3$ residues the index o is different; hence the $R^3$ residues can have none, one or even several $Y(W)_a(Ar)_b$ residues.

If not each $R^3$ substituent in the silicic acid polycondensate has one (or several) $(Ar)_b(W)_aY$— residue(s), those $R^3$ substituents that do not contain this residue or do not contain the maximum number thereof as a rule carry instead the residue through substitution of which the $(Ar)_b(W)_aY$— residue was formed. This residue is hereinafter referred to as $R^1$. Suitable $R^1$ residues are explained in detail in the following discussion concerning the selection of the starting materials; they contain a non-aromatic C═C double bond-containing residue.

The presence of the aromatic residue(s) of the substituents $(Ar)_b(W)_aY$— causes a shift, in particular an increase, of the refractive index of the silicic acid polycondensate as well as of the cured silicic acid polycondensate as compared to corresponding compounds in which this substituent is not present.

Since the invention provides condensates in which the amount of aromatic residues can be controlled, among other factors, by the adjustment of the degree of substitution (value of the index o) as well as by the selection of the number of $R^3$ residues in the condensate the invention provides a material the refractive index of which can be tuned in a simple manner as desired. Due to the fact that the number of $(Ar)_b(W)_aY$— residues is independent of the number of $R^2$ residues, and these residues in turn can be present in (a) freely selectable proportions, and (b) can also be converted in freely selectable proportions into $R^1$ residues carrying organically polymerizable C═C double bonds, as explained below in detail, the invention provides materials in which the refractive index and the mechanical properties can be arbitrarily and very finely adjusted independently of each other.

The inventive silanes of formula (1) and the silicic acid (hetero)polycondensates containing structures of formula (1) can be obtained starting from known silanes. As mentioned above, these silanes have the shared feature of having a $R^1$ residue bonded to silicon by carbon, which contains at least one non-aromatic C═C double bond. These double bonds can be present, for example, as a component of vinyl- or allyl groups or as a component of groups that are accessible to Michael addition, such as (meth)acryl- or norbornenyl groups. Examples of such silanes can be found in the following publications: listed in DE 40 11 044 A1, EP 450 624, DE 44 16 857 C1, DE 196 27198, DE199 10 895 A1, DE 103 49 766 A1, DE 101 32 654 A1, DE 10 2005 016 059 A1, DE 10 2011 054 440 A1, DE 10 2011 053 865 A1 and DE 10 2012 109 685 A1. In addition to silanes having a straight chain or branched organic residue carrying one or two C═C double bonds and 5 to 50 carbon atoms and which is linked via a grouping A with A=O, S, PR", POR" or NHC(O)O to the residue bonded to silicon by carbon, as disclosed in DE 40 11 044 A1, or where the named linkage occurs via an acid amide group, as disclosed in DE 199 10 895 A1, they can, for example, be silanes with a similar structure as the aforementioned, but with an additional hydroxy- or COOH group, as disclosed in DE 44 16 857 C1, or with a phosphorus-containing group, for example a phosphonic acid, as is known from DE 101 32 654 A1. Other examples are named in DE 103 49 766; these silanes have at least two identical or different C═C double bond-containing residues, which are bonded to the carbon-bonded hydrocarbon residue at different intervals to the silicon atom, where at least one of the C═C double bond-containing residues is bonded with the hydrocarbon residue via a coupling group —NH—C(O)O—, —NH—C(O)— or —CO(O)—. And finally, reference shall be made to silanes which contain at least one norbornenyl- or related grouping, such as described in DE 196 27 198 A1.

As a rule, the $R^1$ residue contains at least two carbon atoms, and preferably up to approximately 50, but optionally even more. The organically polymerizable group can thereby be bonded directly, or via a coupling group, to the carbon skeleton of the hydrocarbon-containing residue. Preferably, the organically polymerizable residue contains at least one C═C double bond, frequently also two C═C double bonds. In specific embodiments, it is or contains at least one acrylate- or methacrylate group.

Examples of silanes or silicic acid (hetero)polycondensates to be named are the following known from the state of the art, where the definitions of the residues and indices are taken from the respective publications and are not to be equated with those used for the description of the present invention:

Silanes of the general formula (A):

$\{X_aR_bSi[R'(A)_c]_{(4-a-b)}\}_xB$ (A)

wherein the residues have the following meaning:
X: hydroxy, alkoxy, acyloxy, alkylcarbonyl, alkoxycarbonyl or —NR"$_2$;
R: alkyl, alkenyl, aryl, alkylaryl or arylalkyl;
R': alkylene, arylene or alkylenarylene;
R": hydrogen, alkyl or aryl;
A: O, S, PR", POR" or NHC(O)O;
B: straight chain or branched organic residue that is derived from a compound having at least three C═C double bonds and 5 to 50 carbon atoms;
a: 1, 2 or 3;
b: 0, 1 or 2;
c: 0 or 1;

X: integer, the maximum value of which corresponds to the number of double bonds in compound B minus 1,
and silicic acid polycondensates derived therefrom that were formed by hydrolytic condensation of the silanes of formula (A). Such silanes and polycondensates are disclosed in DE 40 11 044 A1. They fall under the present structural formula (1) with $R^1$ and $R^2$ equal to organically polymerizable residue.

Silanes of general formula (B):

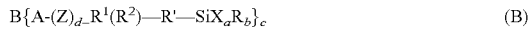

wherein the residues and indices have the following meaning:
A=O, S, NH or C(O)O;
B=a straight chain or branched organic residue having at least one C=C double bond and 4 to 50 carbon atoms;
R=alkyl, alkenyl, aryl, alkylaryl or arylalkyl;
R'=alkylene, arylene, arylenalkylene or alkylenarylene having 0 to 10 carbon atoms respectively, where these residues can be interrupted by oxygen atoms and sulfur atoms or by amino groups;
R'=nitrogen, alkylene, arylene or alkylenarylene having 1 to 10 carbon atoms respectively, where these residues can be interrupted by oxygen atoms and sulfur atoms or by amino groups;
$R^2$=OH or COOH;
X=hydroxy, alkoxy, acyloxy, alkylcarbonyl, alkoxycarbonyl or $-NR''_2$;
R''=alkyl or aryl;
Z=CO or CHR, with R equal to H, alkyl, aryl or alkylaryl;
a=1, 2 or 3;
b=0, 1 or 2;
and silicic acid polycondensates derived therefrom that were formed by hydrolytic condensation of the silanes of formula (B). Such silanes and silicic acid polycondensates are disclosed in DE 44 16 857 C1. They represent structures of formula (1), wherein $R^2$ is a hydroxy group or a carboxylic acid group.

Silanes of general formula (C):

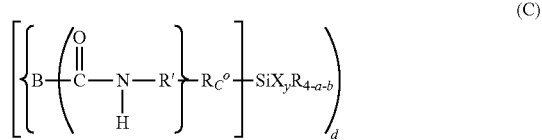

wherein the residues and indices have the following meaning:
B=organic residue having at least one C=C double bond;
R=alkyl, alkenyl, aryl, alkylaryl or arylalkyl;
$R^O$ and R' respectively=alkylene, alkenylene, arylene, alkylenarylene or arylenalkylene;
X=hydroxy, alkoxy, acyloxy, alkylcarbonyl, alkoxycarbonyl or $-NR''_2$ with R'' equal to hydrogen, alkyl or aryl;
a=1, 2 or 3;
b=1, 2 or 3, with a+b=2, 3 or 4;
c=1;
d=1, 2, 3, 4, 5, 6, 7, 8, 9 or 10;
e=2, 3 or 4;
and silicic acid polycondensates derived therefrom that were formed by hydrolytic condensation of the silanes of formula (C). The silanes of formula (C) and the silicic acid polycondensates that can be derived therefrom are disclosed in DE 199 10 895 A1. They fall under structures of formula (1), wherein $R^2$ is an organically polymerizable residue. In the case that b in formula (C) has the meaning of 2 or 3, one or two of the additional bonds of the silicon atom also have the meaning of $R^3$ in formula (1).

Silanes of general formula (D):

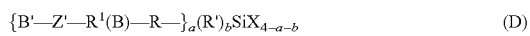

wherein the residues and indices have the following meaning:
R is an alkylene-, arylene- or alkylenarylene group that can be interrupted by one or more oxygen atoms or sulfur atoms or by carboxyl- or amino groups or can carry such atoms/groups on their end facing away from the silicon atom;
$R^1$ is a $Z^1$ substituted alkylene-, arylene- or alkylenarylene group that can be interrupted by one or more oxygen- or sulfur atoms or by carboxyl- or amino groups or carry such atoms/groups on one of their ends;
R' is an alkyl-, alkenyl-, aryl-, alkylaryl- or arylalkyl group;
B and B' can be identical or different; both residues have the meaning of a straight chain or branched organic group having at least one C=C double bond and at least two carbon atoms;
X is a group capable of undergoing a hydrolytic condensation reaction with formation of Si—O—Si-bridges, with the exception of hydrogen and halogen;
Z' has the meaning of —NH—C(O)O—, —NH—C(O)— or —CO(O)—, where the two former named residues are bonded to the B' residue via the NH group while the carboxylate group can point in both directions;
a has the meaning of 1 or 2 and
b is 0 or 1;
and the silicic acid polycondensates derived therefrom, which can be obtained by hydrolytic condensation of the silanes (D). Such silanes and polycondensates are disclosed in DE 103 49 766 A1; they can be subsumed under structure (1) wherein $R^2$ is an organically polymerizable residue.

Silanes of general formula (E):

wherein the groups, residues and indices have the following meaning:
B is an at least divalent, straight chain or branched group having at least one organically polymerizable residue and at least 3 carbon atoms,
X is a residue that can be hydrolytically cleaved from the silicon atom or OH, with the exception of hydrogen and halogen,
R and R' are independently of each other optionally substituted alkyl, alkenyl, aryl, alkylaryl or arylalkyl,
Y is OH or OR',
a is 0, 1, 2 or 3,
b is 0, 1 or 2, where a+b together are 1, 2 or 3,
c is 0, 1 or 2,
d is 0, 1 or 2,
c+d together are 2,
m is at least 1, with the proviso that m is not greater than 1 if a+b has the meaning of 1 or 2,
n is at least 1,
o is 0 or 1, and
p is 0 or 1,
and silicic acid polycondensates derived therefrom that are obtained by hydrolytic condensation of the silanes of formula (E). Silanes of formula (E) and silicic acid polycondensates derived therefrom are disclosed in DE 101 32 654 A1. They fall under structure (A), wherein $R^2$ is a phosphorous-containing residue, for example, a phosphonic acid.

Silanes of general formula (F):

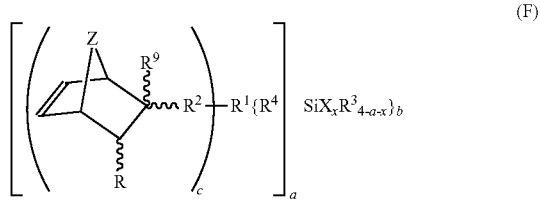

wherein the residues and indices are identical or different and have the following meaning:

R is hydrogen, $R^2-R^1-R^4-SiX_xR^3_{3-x}$, carboxyl, alkyl, alkenyl, aryl, alkylaryl or arylalkyl, $R^1$ and $R^2$ are independently of each other, alkylene, arylene, arylenalkylene or arylenalkylene, $R^3$ is alkyl, alkenyl, aryl, alkylaryl or arylalkyl;

$R^4$ is $-(CHR^6-CHR^6)_n-$ with n=0 or 1, $CHR^6-CHR^6-S-R^5-$, $-C(O)-S-R^5-$, $CHR^6-CHR^6-NR^6-R^5$, $-Y-C(S)-NH-R^5$, $-S-R^5-$, $-Y-C(O)-NH-R^5-$, $-C(O)-O-R^5-$, $-Y-CO-C_2H_3(COOH)-R^5-$, $-Y-CO-C_2H_3(OH)-R^5-$ or $-C(O)-NR^6-R^5$, $R^5$ is alkylene, arylene, arylenalkylene or arylenalkylene, $R^6$ is hydrogen, alkyl or aryl with 1 to 10 carbon atoms, $R^9$ is hydrogen, alkyl, alkenyl, aryl, alkylaryl or arylalkyl;

X is hydroxy, alkoxy, acyloxy, alkylcarbonyl or alkoxycarbonyl;

Y is $-O-$, $-S-$ or $NR^6$,

Z is $-O-$ or $-(CHR^6)_m$ with m equal to 1 or 2;

a is 1, 2 or 3, with b=1 for a=2 or 3 b is 1, 2 or 3, with a=1 for b=2 or 3 c is an integer from 1 to 6, x is 1, 2, or 3 and a+x are 2, 3 or 4, with the proviso that when c=1, $R^4$ must be $-Y-CO-C_2H_3(COOH)-R^5-$ or $-Y-CO-C_2H_3(OH)-R^5-$.

Such silanes and silicic acid polycondensates produced therefrom are known from DE 196 27198.

The silanes or structures of formula (1) according to the invention can be generated by reaction of a silane of formula (0) or of a silicic acid (hetero)polycondensate of structure (0) having a $R^1$ residue bonded to silicon by carbon containing at least one non-aromatic C=C double bond, with a compound (II), where the reaction obeys the following reaction equation:

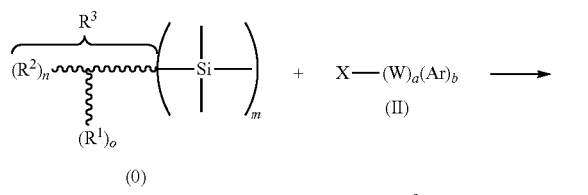

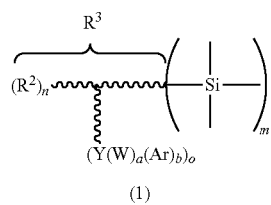

As a rule, the $R^1$ residue contains at least two, and preferably up to approximately 50, optionally also even more carbon atoms, and contains at least one C=C double bond, and more preferably is accessible to Michael addition. In specific embodiments, it is or contains at least one (meth)acryl group, in particular an acrylate- or methacrylate group. The $R^1$ residue can be bonded directly, or via a coupling group, to the carbon skeleton of the hydrocarbon-containing $R^3$ residue.

The term "(meth)acryl . . . " as used herein is understood to mean that it can represent the respective corresponding acryl- or the corresponding methacryl-compound, or a mixture of both. The present (meth)acrylic acid derivatives comprise the acids themselves, optionally in activated form, esters, amides, thioesters and the like.

In formula (II), W, Ar, a and b have the meanings as defined above, and X is selected from HS—, $HNR^4-$ and $HP(O)_eR^4_cZ'_d-$, where Z', $R^4$, e, c and d have the meaning as defined above for formula (1), HN= and HP(O)=. Examples of useable compounds (II) to be named are the following:

Thiophenol, 1-naphthalenethiol, 2-naphthalenethiol, 4-phenylthiophenol, 4-terphenylthiol, 2-, 3-, and 4-thiocresol, N-methyl-4-biphenylamine, N-methyl-1-naphthylamine, N-methyl-2-naphthylamine, carbazole, 4-(3-thienyl)-aniline, 2-aminoanthracene, 2-thiophenemethylamine, aniline, 4-phenylsulfonylaniline, 4-benzylaniline, 1-aminonaphthalene, 2-aminonaphthalene, 6-aminochrysene, 2-, 3- and 4-aminobenzophenone, 3-, 5- and 6-aminoquinoline, pyrrole, 3- or 4-aminoacetophenone, phosphonic acid derivatives such as diphenyl phosphite $H-P(O)(OPh)_2$ or ethyl phenylphosphinate $H-P(O)(OEt)(Ph)$ and phosphine oxides such as diphenyl phosphine oxide $H-P(O)(Ph)_2$. During the reaction, the SH—, NH— or PH group attacks onto the double bond (the former is the known thiol-ene-addition), whereby the $-(W)_a(Ar)_b$ residue becomes bonded via the resulting Y grouping to the thereby forming structure (I).

This reaction can be stoichiometric, i.e. with one mole of compound (II) per mole of $R^1$ residue. However, this reaction can also be substoichiometric, i.e. with less than one mole of compound (II) per mole of $R^1$ residue. In the case of silanes, a silane mixture is thereby obtained from the precursor silane of formula (0) which still carries the residue $R^1$ together with the product silane (1). From this silane or silane mixture, a silicic acid polycondensate can be generated by hydrolytic condensation, which, in the case of the mixture, exhibits structures of formula (0) as well as structures of formula (1). The proportion of compound (II) used in the reaction can therefore allow a very fine adjustment with respect to how high the proportion of Ar in the formed silicic acid (hetero)polysiloxane is, so that the respective values specified therefor above can be fully realized. Alternatively, this adjustment can also be obtained by condensing silanes of formula (1) with silanes that do not contain Ar groups in the aforementioned sense, whereby, for example, they are of formula (0), but can optionally also have a slightly or completely different structure, e.g. silanes of formula (4)

wherein

R' represents an unsubstituted or substituted alkyl- or alkenyl group having preferably 1 to 12 carbon atoms, R" represents a substituted or unsubstituted hydrocarbon residue, which can contain an organically polymerizable or a non-organically polymerizable C=C double bond and is or contains, for example, an alkylene- or an alkenylene group having preferably 2 to 20 carbon atoms and/or the carbon chain of which is interrupted once or several times by arbitrary heteroatoms or coupling groups, such as —S—, —O—, —NH—, —NR$^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)— or —NHC(S)O—, and X is a group that is hydrolysable under hydrolysis conditions, as is known from the state of the art, which can be selected from hydrocarbon residues bonded to the silicon by an oxygen atom, including alkoxides (preferably $C_1$-$C_6$-alkoxy) and acyl residues, halogen atoms such as Cl or Br, amino groups and the like, or wherein X can be a free OH group, a=0, 1, 2 or 3 and b=0, 1, 2 or 3 with the proviso that a+b together=1, 2 or 3.

Depending on the proportion of the silane of formula (1) to the one or to the additional silane(s) of formula (0) or (4) or the like, a silicic acid (hetero)polysiloxane can thereby be produced that contains between >1 and ≤100 mole-% (for b=1), optionally also up to ≤200 mole-% (for b=2) or even more (b=3 or greater) Ar groups per silicon atom.

If the reaction already occurs on the level of the silicic acid (hetero)polycondensate, these can be composed exclusively of structural units (1) or contain any number of structural units (0), which, for example, results from a substoichiometric use of compound (II). This arbitrary proportion can be only just one substituent or R$^3$ residue per silicon atom or can be even greater; however the latter only applies if some or all of the silicon atoms contain two R$^3$ residues. It can, however, also be less, such that not all or only a proportion of e.g. 25, 50 or 75 mole-% of the silicon atoms contain a R$^3$ residue of structure (0). By selecting the amount of compound (II) (stoichiometric or substoichiometric relative to the amount of R$^2$ residues, e.g. 2, 10, 50 or 100 mole-%), and the number of Ar groups per compound (II) it can be tuned as to how high the proportion of Ar groups should be.

A particular advantage of the present invention is therefore that with the appropriate selection of a starting material, which is available in the state of the art, any graduation can be achieved through only one reaction, because with the selection of the starting material (silicic acid polysiloxane of formula (0) or corresponding silane/silane mixture) the proportion of R$^1$ groups per silicon atom can already be defined. By selecting the stoichiometric proportion of compound (II) to R$^3$ residue as well and the amount of Ar groups per compound (II), the ratio of silicon atoms to the number of Ar groups, the ratio of silicon atoms to the number of remaining residues R$^1$ as well as the ratio of the number of Ar groups to the number of the remaining R$^1$ residues can be completely arbitrarily defined. The reaction on the level of the silicic acid polycondensate thereby has the advantage that a finely graduated product range can be obtained starting from only one condensate, and with only one single step per condensate produced.

The non-aromatic C=C double bonds of the R$^1$ residue are groupings that can be subjected to organic cross-linking under the influence of heat, light, ionizing radiation or by redox-induced means (e.g. with an initiator (peroxide or the like) and an activator (amine or the like)) and thereby form polymers (addition polymerization or chain-growth polymerization). The term "polymerizable" or the corresponding noun "polymerization" is therefore understood herein to mean a corresponding polyreaction during which neither cleavage of molecular components nor migrations or rearrangements occur. Examples of R$^1$ are double bonds that are accessible to Michael addition, such as styryles or (meth)acrylic acid derivatives; they can, however, also be vinyl- or allyl groups.

In all cases in which the reaction is performed with a lower molar amount of (II) than R$^1$ residues are present, and the silicic acid (hetero)polycondensates or (in the case silanes are used that have not yet been hydrolytically condensed) silane mixtures therefore still contain unconverted nonaromatic C=C double bonds, these can optionally be subsequently used for other reactions, but in particular for organic cross-linking of the silicic acid polycondensate, which, in the case silanes are used, preferably occurs only after they have been polycondensed. Such a polymerization reaction enables e.g. light-induced subsequent cross-linking of the silicic acid polycondensate through which, for example, in the context of a dental application (e.g. when dental restoration material is used) the silicic acid (hetero) polycondensate or a composite of this condensate can be cured as a matrix with filler particles embedded therein after molding in the mouth of the patient is completed. For this reason, in one embodiment of the invention it is preferred to use a substoichiometric amount of compound (II) and to optionally introduce the desired amount of aromatic Ar groups into compound (II) by using a correspondingly high proportion thereof. However, there are also other routes that allow subsequent organic cross-linking of the inventive silicic acid polycondensate, as described further below.

It may in fact often be favorable to select an amount of compound (II) that is not too low because with the addition of high amounts of (II), not only the expected decrease in the elastic modulus is observed in addition to the refractive index increase, but surprisingly also a flexibilizing effect in the cured materials.

The inventors were further able to observe the surprising effect that in those cases in which a thiol compound is used as compound of formula (II), a matrix-internal stabilization by the thiol bridge occurs, e.g. as comparison to the radical reaction-induced oxidative decomposition that is frequently observed at higher temperatures with classical polymers.

Potential R$^2$ residues present in the starting material are not attacked during the above reaction of the compound of formula (II) of structure (0). They are therefore available as coupling groups in the obtained silane or silicic acid (hetero) polycondensate and can be used to further modify the products. If required, compounds of structure (III) can be added to these coupling groups in a second reaction stage.

In one embodiment of the invention, this option can then be used to subsequently increase the number of organically polymerizable C=C double bonds (nonaromatic C=C double bonds) in the silanes or silicic acid (hetero)polycondensates provided with the —Y—(W)$_a$(Ar)$_b$ grouping in order to further increase the organic cross-linking potential even though these groups were consumed during the first reaction. This is achieved by reaction with a compound of formula (III), where the reaction obeys the following reaction equation:

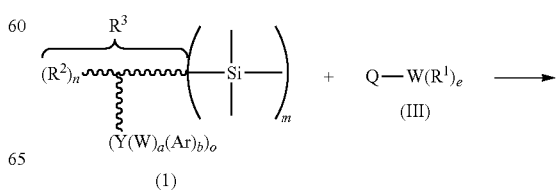

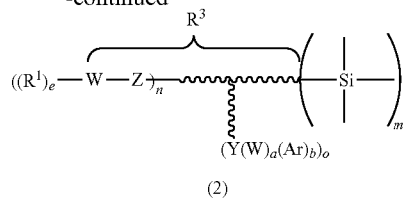

(2)

In a compound of the formula (III), all variants of Q can be selected from an isocyanate group (OCN—) and an epoxy group. Further, in the case $R^2$ is an OH group, Q can be a carboxylic acid group —COOH, which can optionally be present in the activated form, whereas in the case $R^2$ is a carboxylic acid group or a salt or an ester thereof, Q can instead also be an OH-Group. W has the meaning defined above in the context of formula (II), $R^1$ is a straight chain or branched, organically polymerizable group carrying at least one C=C double bond, and e has the meaning of 1, 2, 3, 4 or an even greater number. By attack of Q onto the $R^2$ residue, a coupling group Z is created in the product. In the event of an attack of an isocyanate group onto an COOH group, an acid amide group —C(O)NH— is formed, and in the event of an attack onto an OH group, an urethane group is formed. An ester group is formed from Q=COOH (or an activated form thereof) and $R^2$=OH; likewise, from Q=OH and $R^2$=COOH or an ester or salt thereof, which is, of course, oriented in the opposite direction. With the latter listed variant it must thereby be observed that transesterification occurs if $R^2$ is a carboxylic acid ester. In order to shift the equilibrium to the side of the product, the alcohol component of this ester (R* of $R^2$=COOR*) should preferably be the product of a primary and small alcohol R*OH. If Q is an epoxy group, an ether is formed (with formation of a free hydroxy group) when $R^2$=OH, and an ester when $R^2$=COOH.

Z in the compound or structure (2) therefore has the meaning of a urethane-, acid amide-, ether- or ester group, where the ester group can be located on both ends. The W—$(R^1)_e$ residue is bonded to the hydrocarbon group of the $R^3$ residue via this coupling group.

The aforementioned reactions are preferably performed on already partially or completely precondensed silicic acid (hetero)polysiloxanes. As previously mentioned, it is of course equally possible to produce the respective silanes first and to subsequently subject them to hydrolytic condensation in a known manner. Irrespective of which of the two routes are used, an organic polymerization reaction as described above is carried out only after the resins have been transferred into their final form, for example, into the form of a restoration-/dental replacement material in the mouth of the patient, where the organic polymerization reaction (polyaddition) of the $R^1$ residues is induced preferably by light curing.

The reaction of the silanes or structures (1) with the compound of formula (III) can be stoichiometric, i.e. equimolar, by using one mole of compound (III) (or even an excess thereof) per mole of $R^2$ residue in the silane (1) or in the silicic acid poly condensate structure (1) (in the case an excess is used, it will be separated off after the reaction). Essentially all $R^2$ residues are thereby converted to $(R^1)_e$—W—Z residues. This reaction can instead also be performed substochiometrically. In this case, either a mixture of silanes of formulas (1) and (2) is formed or a silicic acid polycondensate, which contains structures (1) in addition to structures (2).

In a further embodiment of the invention, which can be carried out either as an alternative to the reaction with the compound of formula (III) or combined with the former, where the latter is possible only when during the reaction with the compound of formula (III) only some of the $R^2$ residues were converted, the $R^2$ residues or the remaining residues can be utilized in a further reaction stage to generate an additional organic network, which, however, does not consist of polyadded C—C-groupings. This is enabled by reaction with a compound (IV), as is disclosed in principle in DE 10 2005 018059.

During this reaction, the silanes or structures of formula (1), in which at least some of the $R^3$ substituents contain $R^2$ residues (i.e. n>0, preferably at least 0.2, more preferably at least 0.5), are reacted with a compound (IV), where the conversion obeys the following reaction equation:

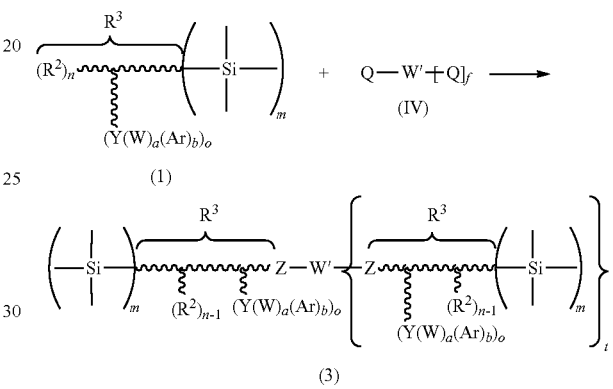

Q in the compound (IV) is selected from —NCO, —OH, an epoxide group or —C(O)X', where —C(O)X' is a carboxylic acid group or an activated carbonyl compound, in particular an acid chloride or an acid anhydride (with X'=—O—C(O)-alkyl or -aryl or -alkylaryl/arylalkyl), and Q can be —NCO or —C(O)X' when in the structure of formula (1) $R^2$ has the meaning of OH and where Q can be —NCO or —OH— when in the structure of formula (1) $R^2$ has the meaning of COOR with R=OH or a salt-forming cation or an ester group. Q can also be part of a cyclic, intramolecular anhydride; in these cases, 2 Q residues form a group —C(O)O(O)C— that is bonded to two carbon atoms of W. W can be a single bond in exceptional cases (namely only when Q are each activated carboxylic acid groups and f is equal to 1, i.e. only in the case in which the compound of formula (IV) is oxalic acid or an activated oxalic acid derivative) and is furthermore a "spacer", i.e. an arbitrary residue with f+1 valences. Preferably, W contains or is a carbon chain, which is optionally interrupted by oxygen atoms, sulfur atoms, carbonyl groups, carboxyl groups, amino groups or amide groups, in particular an alkyl chain having 1 to 60, more preferably 1 to 15 carbon atoms. Instead, W can contain one or several, optionally (one) additional rings containing such carbon chain(s) (cycloalkyl ring, aromatic ring with or without heteroatoms) or have a pure ring structure, e.g. be a phenylene group, a naphthylene group or a diphenylene group. Provided the compound (IV) has one or more aromatic groups, it is thereby possible to further increase the refractive index; therefore, this embodiment is particularly preferred. The rings or the carbon chains can further be optionally substituted provided their substituents do not interfere with the reaction between Q and $R^2$. An example hereof is a cyano- or tricyano group. f is preferably 1, but can also be 2, 3, 4, 5, or 6. For example, di-, tri- or tetra anhydrides, -carboxylic acids (optionally activated or activatable), -isocyanates or -alcohols are commercially available on a large scale. Natural oligomers, such as sugar molecules, can also be used in the present invention. In exceptional cases, f can even represent a higher number than 6.

By attack of several Q residues onto several $R^2$ residues a product is formed in which at least two silanes or structures of formula (1) are linked together via two coupling groups Z and the "spacer" W'. In the event of an attack of an isocyanate group onto a COOH group, an acid amide group —C(O)NH— is formed, and in the event of an attack onto an OH group, a urethane group is formed. An ester group is formed from Q=COOH (or an activated form thereof) and $R^2$=OH; likewise, from Q=OH and $R^2$=COOH or an ester or salt thereof, which is, of course, oriented in the opposite direction. With the latter listed variant, it must thereby be observed that transesterification occurs if $R^2$ is a carboxylic acid ester. In order to shift the equilibrium to the side of the product, the alcohol component of this ester (R* of $R^2$=COOR*) should preferably be the product of a primary and small alcohol R*OH. If Q is an epoxy group, an ether is formed (with formation of an adjacent OH group if $R^2$=OH), and an ester if $R^2$=COOH.

Z in the compound or structure (3) therefore has the meaning of a urethane-, acid amide-, ether- or ester group, where the ester group can be located on both ends.

The compound of formula (IV) can be mirror-symmetrical, but is not required to be.

It is readily apparent that the reactions with the compounds (III) or (IV) differ only in the respect that compound (IV) contains several Q residues and is therefore suitable for linking several silanes or structures with substituents or residues (3), while compound (III) introduces the $R^1$ residue into the $R^3$ substituent or residue via the same coupling reaction and thereby enables cross-linking of C=C double bonds via a polyaddition reaction (polymerization reaction in the sense of "chain-growth polymerization or "addition polymerization"), as is known from the state of the art. This also makes apparent that either the one or the other of the reactions can be selected as needed, or a combination of both reactions, where an appropriate deficit must be used of at least the compound (III) or (IV) which is to be reacted first with the silane or the structure (1). By the selection of the corresponding proportions (equivalents), the product properties can be very finely tuned in this respect as well. The general rule thereby applies: If the amount of compound (IV) is selected to be relatively high, the previously liquid resin can harden, which is not always desirable; therefore, in a number of cases an amount of 0.2 mole per $R^2$ residue can be advantageous, especially when during the reaction with compound (II) a large number of the double bond-containing $R^1$ residues have remained and/or such residues have been reintroduced/are simultaneously reintroduced by reaction with the compound (III), so that curing is still possible later. If, however, the amount of $R^1$ residues is low for one and/or the other reason or $R^1$ residues are not available at all, thus the resin cannot be post-cured by a polymerization reaction of the C=C double bonds of these residues, it may be desirable to select a high amount of compound (IV) in order to effect cross-linking by this route and thereby cure the silicic acid (hetero)polycondensate. In general, when high amounts of the compound (IV) are used (e.g. close to or exactly (c+1) mole per mole of silane having a $R^3$ substituent or per $R^3$ substituent in the silicic acid (hetero)polycondensate) a purely organic post-curing of the resin systems can be achieved in this manner without some of the $R^1$ residues remaining unconverted or $R^1$ residues having to be reintroduced by reaction with compound (III) for this purpose.

A special form of post-curing does not (or not only) as such effect the polymerization reaction (polyaddition) of the C=C double bonds, as explained above. It is namely also possible to react the silanes or silicic acid polycondensates having said double bonds with di- or higher amines or di- and higher thiols via Michael addition (thiol-ene-reaction or the analogous reaction with amines). Di-, tri-, tetra- or even higher functionalized amines or mercaptanes are suitable for this purpose, whereby the reaction with amines succeeds (only) if the C=C double bonds are present in activated form, for example, as acryl- or methacryl groups (including (meth)acrylate groups). This enables cross-linking to occur via the aforementioned polyfunctional mercaptanes or amines in place of cross-linking by light-induced organic polyaddition ("chain growth polymerization") as mentioned above. Examples of polyfunctional thiols are: trimethylolpropane tri(3-mercaptopropionate) (TMPMP); trimethylolpropane trimercaptoacetate (TMPMA); pentaerythritol tetra (3-mercaptopropionate) (PETMP); pentaerythritol tetramercaptoacetate (PETMA); glycol dimercaptoacetate; glycol di(3-mercaptopropionate); ethoxylated trimethylolpropane tri(3-mercaptopropionate); biphenyl-4-4'-dithiol; p-terphenyl-4,4"-dithiol; 4,4'-thiobisbezenthiol; 4,4'-dimercaptostilbene; benzene-1,3-dithiol; benzene-1,2-dithiol; benzene-1,4-dithiol; 1,2-benzenedimethanethiol; 1,3-benzenedimethanethiol; 1,4-benzenedimethanethiol; 2,2"-(ethylenedioxy)diethanethiol; 1,6-hexanedithiol; 1,8-octanedithiol, and 1,9-nonanedithiol. The same can be achieved if, instead of the aforementioned thiols, amines are used, provided, as mentioned, the C=C double bonds are present in activated form. Examples of polyfunctional thiols are: diaminoacetone, diaminoacridine, diaminoadamantane, diaminoanthraquinone, benzidine, diaminobenzoic acid, phenylenediamine, diaminobenzophenone, diaminobutane, diaminocyclohexane, diaminodecane, diaminodicyclohexylmethane, diaminomethoxybiphenyl, diaminodimethylhexane, diaminodiphenylmethane, diaminododecane, diaminoheptane, diaminomesitylene, diaminomethylpentane, diaminomethylpropane, naphtyhlenediamine, diaminoneopentane, diaminooctane, diaminopentane, diaminophenanthrene, diaminopropane, diaminopropanol, diaminopurine, diaminopyrimidine. As a rule the thiol addition is performed in the presence of an initiator, as known from the state of the art, while the amine addition is possible even without an initiator.

The mentioned post-curing (polyaddition) can be performed in place of the polymerization reaction of the C=C double bonds (the "chain growth polymerization"); a slightly looser organic network thereby forms because S-(hydrocarbon)-S-bridges or N-(hydrocarbon)-N-bridges are formed. However, it can also be performed additionally by selecting the amount of di- or poly thiols or di- or polyamines in such a way that C=C double bonds remain in the resin that can subsequently be postcured in a conventional manner.

During cross-linking, other properties, such as the length of the molecular chains between the cross-linking sites and the remaining amounts of free reactive groups can furthermore be adjusted, for example, by addition of variable amounts of di-, tri- and/or tetra isocyanates, which can react with respective free Q groups. Through the use of bis-, tris- or even higher functional compounds as reaction partners of formula (IV) linkages are created via bridges with selectively adjustable lengths (the length adjustment is determined by the distance of the reactive Q groups in the molecule). The reaction with isocyanates is an example hereof: The following may be employed: e.g. dicyclohexylmethane diisocyanate, hexamethylene-1,6-diisocyanate, hexamethylene-1,8-diisocyanate, diphenylmethane-4,4-diisocyanate, diphenylmethane-2,4-diisocyanate, 2,4-toluene diisocyanate, 2,6-toluene diisocyanate, triphenylmethane-4,4',4"-triisocyanate, 3-isocyanatomethyl-3,5,5-trimethylcyclohexyl diisocyanate, or tris(p-isocyanatophenyl)thiophosphate. Provided the $R^2$ residues represent a hydroxy group, such cross-linking can e.g. also be performed using a di-, tri-, tetra or polyfunctional, optionally activated (e.g. present in the form of an anhydride) carboxylic acid in place of the di-, tri- or tetrapolyisocyanate, while in the case said residue is a free carboxylic acid residue, or a salt or ester thereof, the cross-linking can instead occur using a di-, tri-, tetra or polyfunctional alcohol.

In general, the inventive resins are used for dental purposes in particle-filled form. Suitable fillers are, for example, those described in DE 196 43781, DE 19832965, DE 10018405, DE 1041038, DE102005018351, DE102005061965.7 and in particular in DE102011054444.5. These fillers are examples of principally possible fillers for producing composites. It is, however, preferred that classical, commercially available dental glass fillers, e.g. from the company Schott, form at least a significant portion of the filler (preferably above 50 wt.-%, more preferably above 75 wt.-%). In these embodiments, the remainder may consist of e.g. fillers as those named in the above publications. By resorting to the preferred dental glass filler, optionally in combination with additional fillers as described above, it is possible to adjust the refractive indices of the inventive resin systems with those of the filler/dental glass to such an extent that they are almost (or, preferably, even completely) identical. Refractive index differences of $\Delta_{nD}$ in the region of ±0.001, often of ±0.0005 can be achieved. In this way, the desired and also necessary translucency of the inventive composites is obtained, which can thus be utilized as highly aesthetic dental materials.

Provided the aforementioned reactions are conducted using silane compounds, they can be subsequently subjected to hydrolytic condensation, as already mentioned. Such a condensation reaction can be performed using either a single inventive silane compound or using a mixture of several silane compounds, which are formed by the inventive reaction(s) with a deficit of the respective compound (II), (III) or (IV). In both cases, additional known silanes or alkoxy metal compounds, such as alkoxides of aluminum, titanium, boron or zirconium or of other transition metals, can be introduced by condensation as needed. By addition of silanes with four hydrolyzable groups, such as tretraalkoxy silanes and/or alkoxy metal compounds, the inorganic network can, for example, be stabilized and the number of the organic substituents "diluted," while the addition of silanes having two or three such hydrolyzable groups and one or two substituents bonded to silicon by carbon allows various modifications to be performed. Thus, a higher number of silane-bonded alkyl groups modifies the mechanical properties of the final cured silicic acid polycondensate, while silane-bonded hydrocarbon groups having reactive substituents allow the option of additional reactions. Silane-bonded hydrocarbon groups containing organically polymerizable C=C double bonds can in turn be added in order to increase the organic cross-linkability in the event that under specific circumstances the reaction of the silane or structure (1) with compounds of formula (II) and/or (III) are either not sufficient for this purpose or should not be performed for other reasons.

In every case, it is preferred that hydrolytic condensation of the silanes is performed before the organic cross-linking reactions are carried out, be it by polymerization of the $R^1$ residues, or by reaction of compounds (1) with a compound (IV). The opposite route is, however, not excluded; under specific circumstances, it can be the more suitable route.

The novel functionalized resin-/matrix systems described in the present application provide materials which, due to their special properties (finely adjustable refractive index with adjustable elastic modulus and optionally matrix-internal stabilization by thiol bridges) can, on the one hand, be used directly and can therefore be suitable for special optical applications, e.g. due to the refractive index increase achieved by introduction of the —Y—$(W)_a(Ar)_b$ groupings, and, on the other hand, precisely because of the fine tunability of the refractive index with fillers can, on the other hand, be processed composites for use in, for example, the dental field in which the refractive indices of the resin and filler can be selected to be almost or completely identical as needed so that high translucency is achieved. The resins are characterized by the possibility of producing plastically processable composites with a very high filler content (up to above 85% by mass, in individual cases even up to above 89% by mass and thus above 80% by volume). In the cured form, they exhibit an elastic modulus with high strength that can be adjusted to the respective application, high abrasion resistance, very low shrinkage, excellent aesthetics (adjustable translucency up to complete translucency), they do not contain monomers and are thus highly biocompatible. Due to the partially observed matrix-internal stabilization (prevention/reduction of radical reaction-induced oxidative decomposition of —S-group-containing resins) they can also be used at elevated temperatures (e.g. up to approx. 100° C.).

The utilization of the materials according to the invention is highly diverse; including use for various purposes in the form of bulk materials, composites, cements, adhesives, casting compounds, coating materials, adhesion promoters, to manufacturing or priming of fillers and fibers, and for processing in the (reaction)extruder. In particular, the utilization for (dental) medical and (micro)optical and (micro) electronic applications is of significance.

The particularly preferred utilization is in
 the dental field, e.g. as a restoration/dental replacement (crowns, bridges, inlays, onlays, veneers, dental prosthesis, implant structures, abutments) or prophylaxis material, adhesive, ionomer cement, in prosthetics and as implant material,
 in the field of multi-photon polymerization (provided the material contains $R^1$ residues): The liquid resin can be treated in a bath with focused laser beams in such a way that curing occurs only in the focus of the laser beam by polymerization of the C=C-groups in the $R^1$ residues, which allows the production of a hard body of any form and exact dimensions within the bath. This application is assigned to the optical field.

The present invention further has the following advantages:
 The described addition reactions are usually very fast and simple reactions under mild conditions (in part without catalyst or with very low catalyst concentrations) without any additional work-up/purification steps, which lead to the higher refractive structures (conversion to compound or structure (1)), the structures with increased cross-linking potential with increased refractive index (reaction of compounds or structures (1) with a compound (III)) or the cross-linked structures with optionally further increased refractive index (reaction of compounds or structures (1) with a compound of formula (IV)). The following applies: reaction of the compounds or structures of formula (0) with the compound (II), i.e. a HS- or HNR-addition to a C=C double bond is performed without a catalyst, at least in the preferred cases in which this group is activated, e.g. by its integration into a (meth)acryl structure. The required measures are known to those skilled in the art.

The invention allows to tune the refractive index to e.g. any commercially available filler starting from already existing silanes and resin systems, due to their aforementioned almost continuous modifiability, in particular as a result of the fine tunability of the refractive index and elastic modulus as mentioned above; therefore there is no need to resort to specially adapted and thus expensive fillers in order to generate a desired, usually extremely high translucency. This enables in the dental field, on the one hand, to realize the required aesthetics of dental direct/indirect restoration/dental replacement materials, while, on the other hand, the achievement of complete transparency enables optical applications. Moreover, as mentioned above, the mechanical properties, e.g. the elastic modulus, can be tuned to the required values independent of the optical properties.

It is important that materials used in the dental field are not able to trigger allergic reactions. It is known that some (meth)acrylate-based monomers are problematic from a toxicological point of view; therefore, they must generally be omitted in the aforementioned applications. To the extent, however, the materials of the present invention contain (meth)acryl groups, for example, in the form of $R^1$ residues or as part of $R^1$ residues, there is no threat, because in any case they are bonded to the inorganic polymer structure (on the basis of inorganic cross-linking via Si—O—Si bridges) in the resin and are thus not present in monomeric form and cannot leach from the dental body in either the non-cured state (in which the resins could potentially be applied for dental purposes) or in the post-cured state (e.g. by light-induced cross-linking of the C=C double bonds in the mouth of the patient). In addition, it must be noted that these considerations by no means exclude the option of adding organic monomers to the inventive silanes, silicic acid (hetero)polycondensates and composites if required.

Of particular importance is the possibility of the very simple, almost continuous modification and thus fine tunability of the inventive silicic acid (hetero)polycondensates or the composites that can be produced therefrom, whereby the invention starts from resin systems that already exist in the state of the art (optionally silanes instead) and provides those of skill in the art with a selection of suitable materials from this group.

The first, or only, reaction is performed with a reaction partner that usually has a simple chemical structure and is therefore cost-effective; mild reaction conditions can be selected and additional work up or purification steps are necessary only in exceptional cases.

In the following, the invention will be explained in more detail on the basis of exemplary embodiments.

EXEMPLARY EMBODIMENTS

Example Ia. Synthesis of Base Resin System 1 with a Coupling Group $R_2$ (=OH) (Production According to DE 4416857)

To 125.0 g (0.503 moles) of 3-glycidyloxypropylmethyldimethoxysilane (MW=236) triphenylphosphine as catalyst, BHT as stabilizer and then 47.35 g (0.550 moles) methacrylic acid are added dropwise in a dry atmosphere and stirred at 80° C. (approx. 24 h). The reaction can be followed by the decrease of the carboxylic acid concentration by means of acid titration and by the epoxide conversion by means of Raman spectroscopy/epoxide titration. The band characteristic of the epoxy group of epoxy silane appears in the Raman spectrum at 1256 cm$^{-1}$. After addition of acetic acid ester (1000 mL/mole silane) and $H_2O$ for hydrolysis with HCl as a catalyst, the reaction is stirred at 30° C. After approx. several days of stirring, the work-up is performed by repeated shaking out with aqueous NaOH and water and filtration through hydrophobized filters. The reaction is first spun off and then drawn off under an oil pump vacuum. The result is a liquid resin without use of reactive diluters (monomers) with a very low viscosity of approx. 3-5 Pa·s at 25° C. and 0.00 mmoles $CO_2H$/g (no free carboxyl groups) and a refractive index $n_D$ of approx. 1.477.

Example Ib. Synthesis of Base Resin System 2 without a Coupling Group $R_2$ (Preparation According to DE 4011044)

To 178 g (0.60 moles) of trimethylolpropane triacrylate (TMPTA), dissolved in acetic acid ester (1 L/mole TMPTA), 90.2 g (0.50 moles) of mercaptopropylmethyldimethoxysilane and ethanolic KOH with 5.0 mmoles KOH are added dropwise under argon with stirring (with cooling so that the temperature remains below 30° C.). The reaction mixture is further stirred for several minutes at room temperature. The completion of the reaction (thiol addition) can be monitored by means of the iodine-mercaptane test. After addition of $H_2O$ for hydrolysis/condensation with HCl as catalyst, the reaction is stirred at room temperature. Work-up is performed after approx. several days of stirring by repeated shaking out with water and filtering through hydrophobized filters. The reaction is first spun off and then drawn off under an oil pump vacuum. A liquid resin results.

Example IIa. Synthesis of the Example Series 1-1. Reaction Stage with Coupling Group $R^2$ (=OH)

Basic Reaction Principle:

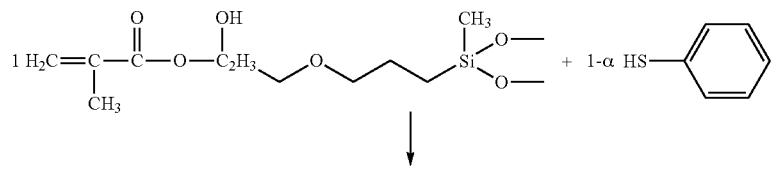

-continued

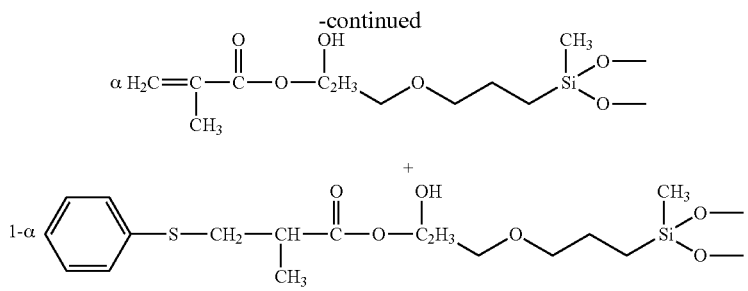

Example IIa (1−α=0.2)

To 26.8 g (0.10 moles) of base resin system 1, 2.20 g (0.020 moles) of thiophenol is added dropwise with stirring. The reaction can be followed e.g. by means of NMR. A liquid resin results with a viscosity of approx. 5.8-6.0 Pa·s at 25° C. and a refractive index $n_D$ of approx. 1.493. Additional work-up is not required.

Example IIa-2 (1−α=0.4)

To 39.7 g (0.15 moles) of base resin system 1, 6.61 g (0.079 moles) of thiophenol is added dropwise with stirring. The reaction can be followed e.g. by means of NMR. A liquid resin results with a viscosity of approx. 7.0-7.2 Pa·s at 25° C. and a refractive index $n_D$ of approx. 1.506. Additional work-up is not required.

Example IIa-3 (1−α=0.45)

To 119.7 g (0.45 moles) of base resin system 1, 22.3 g (0.203 moles) of thiophenol is added dropwise with stirring. The reaction can be followed e.g. by means of NMR. A liquid resin results with a viscosity of approx. 7 Pa·s at 25° C. and a refractive index $n_D$ of approx. 1.508. Additional work-up is not required.

It is to be noted that the refractive index has increased only slightly (by 0.002) as compared to the product of Example IIa-2 due to the slightly increased thiophenol amount. It can thus be very finely adjusted.

It is apparent from the comparison of the Examples Ia (comparator; starting material) 1a and 1b that the refractive index can be finely adjusted via the thiophenol amount: It can be seen that when 20 mole-% thiophenol is used as compound (II), a slight increase occurs as compared to the base resin system 1, with continues to increase when the molar amount of compound (II) is doubled.

A liquid resin is formed in all three examples. Its viscosity increases only slightly from Example IIa-1 to IIa-3.

Example IIb. Synthesis of the Example Series 2-1. Reaction Stage with Coupling Group $R^2$ (=OH)

Basic Reaction Principle:

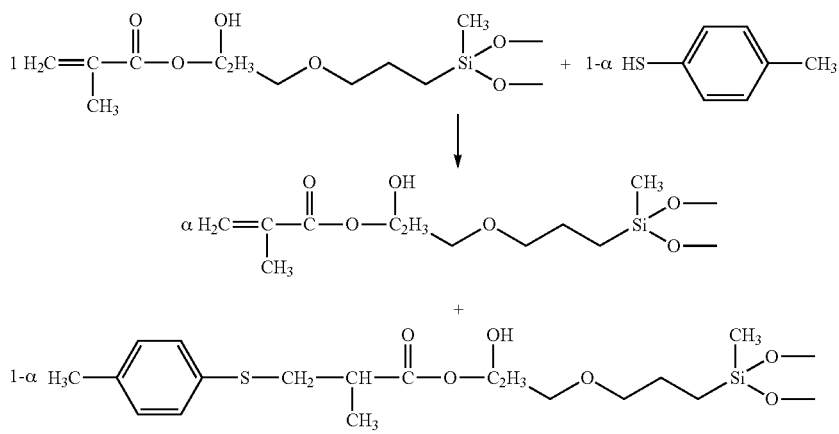

The following components are used for 1−α=0.4: To 2.65 g (0.01 moles) of base resin system 1, 0.50 g (0.0044 moles) of methylbenzenethiol is added dropwise with stirring. The reaction can be followed e.g. by means of NMR. A liquid resin results at 25° C. and a refractive index $n_D$ of approx. 1.506. Additional work-up is usually not required.

Example IIc. Synthesis of the Example Series 5-1. Reaction Stage (with Coupling Group $R_2$ (=OH))

Basic Reaction Principle:

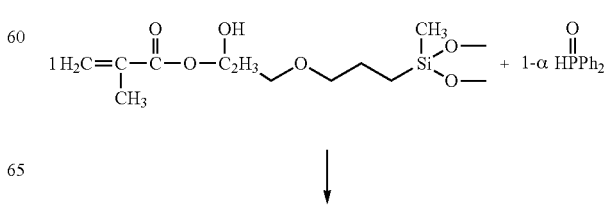

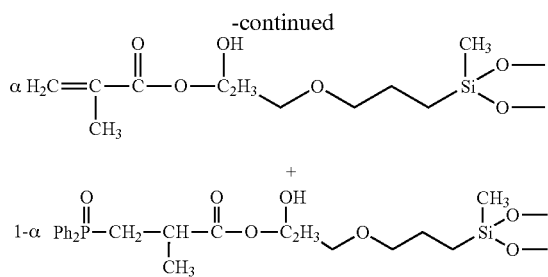

Example IIc (1-α=0.2)

To 16.0 g (0.0615 moles) of base resin system 1, 2.48 g (0.0123 moles) of diphenylphosphine oxide and 0.2 mL of 1,8-diazabicyclo[5.4.0]undec-7-ene (DBU) are added as a catalyst while stirring. The resulting reaction mixture is stirred at ≈50° C. until complete addition. The reaction can be followed e.g. by means of NMR. Following usual work-up e.g. in acetic ester (shaking out with water, filtration through hydrophobized filters, spinning off and then drawing off under an oil pump vacuum) a liquid resin results with a viscosity of approx. 37 Pa·s at 25° C. and a refractive index $n_D$≈1.500. The refractive index of the product of this Example is increased as compared to the refractive index of the Example IIa-1 ($n_D$≈1.493, reaction of base resin system 1 with 0.2 molar amounts of HS-Ph; see Example series 1) with likewise 0.2 mole amounts of the adduct $HP(O)(Ph)_2$, i.e. the refractive index can be adjusted on a higher level. This is due to the presence of two phenyl groups per added molecule. The coupling group $R_2$=OH is not attacked during this reaction and can therefore be used for further addition of C=C-containing compounds (e.g. according to Example IIIa-1; see Example series 4).

Example IId. Synthesis of the Example Series 3-1. Reaction Stage (without Coupling Group $R^2$)

Basic Reaction Principle:

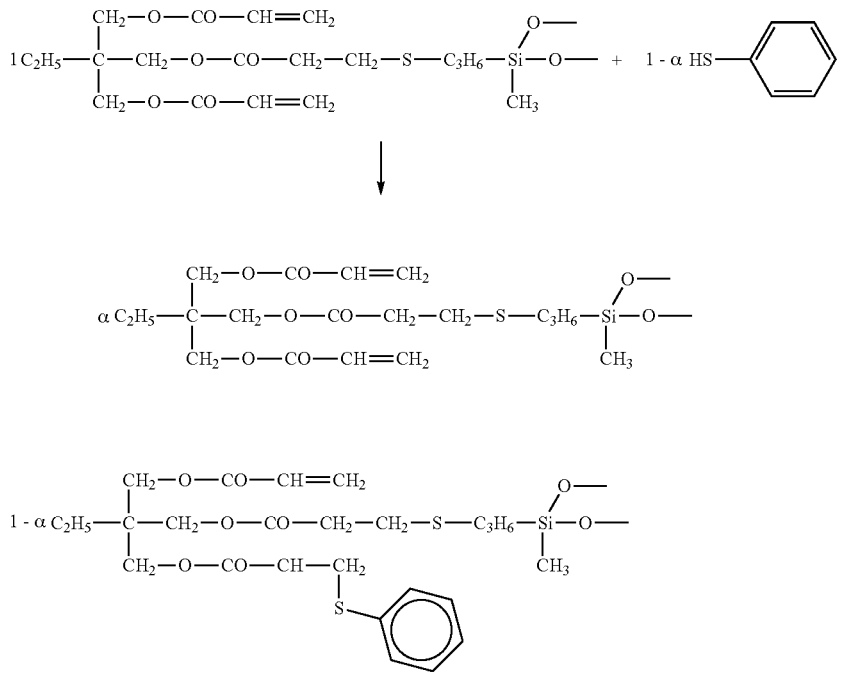

The base resin system 2 (product of the Example Ib) was reacted with different amounts of thiophenol, where, however, care was taken to ensure that the molar amount (1−α) of thiophenol was below that of the silicon residues.

Example IIIa. Synthesis of the Example Series 4-2. Reaction Stage (with Coupling Group $R^2$ (=OH) and Y=—NCO))

Basic Reaction Principle:

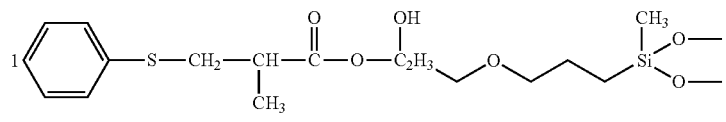

+

-continued

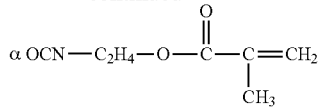

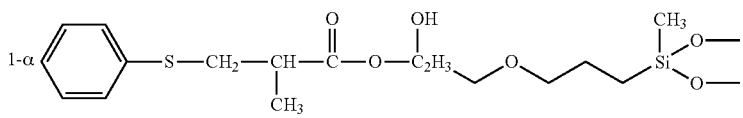

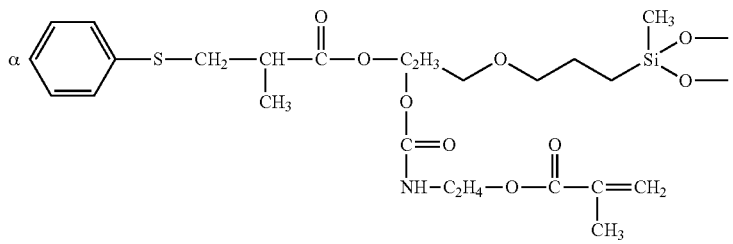

Example IIIa-1 (α=0.8)

To 15.4 g product from Example IIa-2 (0.05 moles) and 0.043 g BHT (2,6-di-tert-butyl-4-methyl phenol), 6.21 g (0.04 moles) of methacrylic acid-isocyanatoethylester (0.8 moles per mole of silicon-bonded $R^3$ residue) are added dropwise in a dry atmosphere at 30° C. and further stirred at 30° C. The reaction can be followed e.g. by the decrease of the OCN band by means of the IR spectrum. The band characteristic of the OCN group appears in the IR spectrum at 2272 cm$^{-1}$. A liquid resin results with a viscosity of approx. 36 Pa·s at 25° C. and a refractive index $n_D$ of approx. 1.502. Further work-up is not required.

Example IIIa-2 (α=0.8)

To 82.1 g from Example IIa-3 (0.26 moles) and 0.23 g BHT, 32.3 g (0.208 moles) of methacrylic acid isocyanatoethylester (0.8 moles per mole of silicon-bonded $R^3$ residue) are added dropwise in a dry atmosphere at 30° C. with stirring and further stirred at 30° C. The reaction can be followed e.g. via the decrease of the OCN band by means of the IR spectrum. The band characteristic of the OCN group appears in the IR spectrum at ≈2272 cm$^{-1}$. A liquid resin results with a viscosity of approx. 37.6 Pa·s at 25° C. and a refractive index $n_D$ of approx. 1.5044.

Of note is that the refractive index is slightly increased (by 0.0024) as compared to the product of Example 4a due to the slightly increased amount of thiophenol.

B. Preparation of Composite

B1. Inventive Composite on the Basis of the Resin from Example IIIa-1

Dental glass from the company Schott with the designation GM27884 ($n_D$=1.53) and the specification UF0.7 (primary particle size of 0.7 μm) is first incorporated into the resin of Example IIIa-1 by means of a three roll mill. Subsequently, dental glass with the specification K6 (primary particle size of 3 μm) is incorporated using a planetary mixer. The glasses were added in a weight ratio of 1:2 (glass of specification UF0.7 to glass of specification K6). The total amount of glass in the composite was 70 wt.-%.

B2. Inventive Composite on the Basis of the Resin from Example IIIa-1

Example B1 was repeated with the difference that dental glass from the company Schott with the designation GM32087 ($n_D$=1.52) and the specification UF0.4 (primary particle size of 0.4 μm) was used and dental glass with the specification K6 (primary particle size of 3 μm).

B3. Comparative Composite on the Basis of Base Resin System 1

Example B2 was repeated with the difference that instead of the resin of Example IIIa-1, the base resin system 1 served as composite matrix.

C. Mechanical and Optical Data after Curing

Polymerization/Curing of Different Resin Systems and Composites as Compared to the Underlying Base Resin The resins from the example series or the base resin system 1 and the composite resulting therefrom were each placed into a rod form (2×2×25 mm$^3$) together with 1% Lucirin TPO. The (meth)acrylate groups were converted by photo-induced radical polymerization, causing the resin to cure. By means of 3-point bending test on the universal testing machine Z100 of Zwick GmbH & Co. KG, the module of elasticity, the fracture strength and the deflection up to fracture of the resultant rods is determined after 1.5 days of storage at 40° C. Following the corresponding production of plate-shaped test bodies, the refractive index is determined by means of a refractometer. The shrinkage values are obtained by means of a buoyancy method in the context of the photo-induced radical polymerization (15 min/1 day after irradiation). The composites with 1% Lucirin TPO are placed in a mold (h=2 mm; d=18 mm), and cured in the context of photo-induced radical polymerization. The translucency is determined by means of a spectrophotometer Color i7 from x-rite.

TABLE 1

| Resin system | Fracture resistance [MPa] | Elastic modulus [GPa] | Deflection [mm] | Refractive index $n_D$ | Shrinkage [Vol.-%] 15 min/1 day |
|---|---|---|---|---|---|
| Base resin-system 1 (comparator) | ≈89 | ≈1.94 | ≈3.2 | 1.504 | 5.2/5.8 |
| 1. Reaction stage (with coupling group $R_2$ (=OH)) | | | | | |
| IIa-1 | ≈71 | ≈1.43 | ≈3.3 | ≈1.519 | n.d. |
| IIa-2 | No realistic values, since very high deflection | | | ≈1.525 | 4.0/4.1 |
| IIc-1 | ≈94 | ≈2.22 | ≈2.8 | 1.519 | |
| 2. Reaction stage (with coupling group $R_2$ (=OH) and Y = —NCO)) | | | | | |
| IIIa-1 | ≈110-116 | ≈2.36-2.42 | ≈2.54-2.71 | ≈1.524 | 4.7/5.7 |

(For multiple measurements, the values shown in the table are mean values unless a range is specified)

When the compound of formula (II) is added in the 1st reaction stage not only the expected decrease in the elastic modulus and a significant reduction in shrinkage is observed in addition to the refractive index increase, but surprisingly a strongly flexibilizing effect on the cured material is also found (especially with a high proportion of (II)).

In contrast, the strength and elastic modulus (despite the reduced number of double bonds resulting from addition to some of the existing double bonds) during reaction IIc-1 are even slightly higher than those of the underlying base resin system 1.

The refractive index is significantly increased in the 1st reaction stage in all cases.

The cured materials of the 2nd reaction stage (addition of a compound of formula (III))—even with a high proportion of previously added compounds (II) (with a resulting very low organic networking potential and the resulting flexibilzing effect and reduced fracture strength)—surprisingly also yield a hard material with high strength and increased refractive index with significantly improved mechanical data and reduced shrinkage, as compared to the underlying base resin system (here base resin system 1), while the refractive index is significantly increased.

TABLE 2

| Composite on the basis of | Amount (wt.-%) | Fillers Type/ratio of fillers to each other | Fracture strength [MPa] | Elastic modulus [GPa] | Deflection [mm] | Translucency [%] |
|---|---|---|---|---|---|---|
| B3 | 70 | GM27884/ UF0.7:K6 = 1:2 | ≈131 | ≈6.95 | ≈0.73 | 38 |
| After 2nd reaction stage (with coupling group $R_2$ (=OH) and Y = —NCO)) | | | | | | |
| B1 | 70 | GM27884/ UF0.7:K6 = 1:2 | ≈151 | ≈7.92 | ≈0.71 | 61 |
| B2 | 70 | GM32087/ UF0.4:K6 = 1:2 | ≈147 | ≈8.19 | ≈0.67 | 58 |

The refractive index of the cured resin system IIIa-1 is exactly between those of the two fillers used. Both composites (B1. and B2.) on the basis of the modified resin system IIIa-1 yield, with the same filler amount/type/ratio, a significant increase in translucency with simultaneous increase in strength and elastic modulus as compared to the composite on the basis of the unmodified base resin system-1 (comparator Example B3.). Composites are thereby made accessible that have high translucency and strength at the same time.

What is claimed is:

1. Compound of formula (1), (2), or (3), or silicic acid (hetero)polycondensate comprising structures of formula (1), (2), or (3)

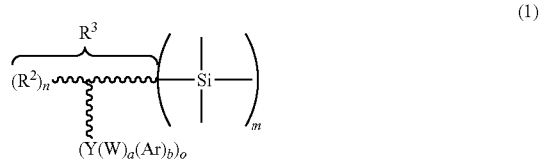

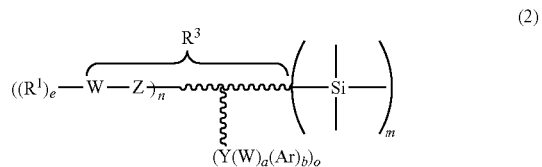

-continued

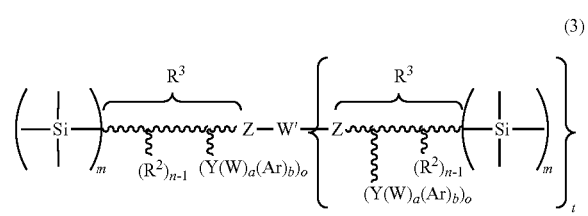

wherein
R² is a hydroxy group or a free carboxylic acid residue or a carboxylic acid ester derived therefrom or a salt derived therefrom,
R³ denotes a residue having a hydrocarbon-containing branched or unbranched backbone which is bonded to silicon by carbon, and can be arbitrarily interrupted by heteroatoms or coupling groups or by other heteroatom-containing groups, where the zigzag line purely schematically denotes the hydrocarbon-containing backbone,
the three not more closely characterized bonds of the Si-atom represent additional residues bonded to the silicon atom, selected from residues that can be hydrolyzed from silicon, hydroxy groups and residues bonded to silicon by carbon, which can have the same meaning as R³ or can have a different meaning deviating therefrom, with the proviso that in case of a compound of formula (1), (2) or (3), the residues are selected such that the silane can subsequently be subjected to hydrolytic condensation or represent oxygen bridges to further silicon atoms and/or other metal atoms if the structure (1) is part of a silicic acid (hetero)polycondensate,
the residue Y is either divalent and then has the meaning of —S—, —NR⁴— or —P(O)(R⁴)$_c$(Z')$_d$— with Z'=OR⁴, c=0 or 1, d=0 or 1 and (c+d)=1, or trivalent and has the meaning of —N= or —P(O)=,
R⁴ represents a hydrocarbon-containing residue and in the residue —NR⁴— can in addition have the meaning of hydrogen,
W is a substituted or unsubstituted hydrocarbon residue, the chain of which can be interrupted by —S—, —O—, —NH—, —NR⁴—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—,
Ar is a residue that carries at least one aromatic group which is unsubstituted or which is substituted with one or more residues, where the aromatic groups do not carry substituents, which are selected from boronic acid-, a carboxylic acid-, a phosphine acid-, a phosphonic acid- and a sulfonic acid group as well as from hydroxy groups,
the index b=1, 2, or 3,
the index m is 1, 2 or an integer greater than 2,
the index n is 0, 1, 2 or greater than 2 and
the index o is 1 or 2 or greater than 2,
Z is selected from urethane-, acid amide-, ether- and ester groups, R¹ is a straight chain or branched, organically polymerizable group carrying at least one C=C double bond and e is 1, 2, 3, 4 or an integer greater than 4,
W', in the case that both Z groups represent ester groups which are bonded to W' via the carboxyl-carbon atom, can be a single bond and is otherwise a carbon chain optionally interrupted by oxygen atoms, sulfur atoms, carbonyl groups, carboxyl groups, amino groups or amide groups, and f=1, 2, 3, 4, 5 or 6 or greater than 6.

2. Silicic acid (hetero)polycondensate comprising structures of formula (1), (2), or (3) as claimed in claim 1, further comprising a particulate filler dispersed therein.

3. Silicic acid (hetero)polycondensate comprising structures of formula (1), (2), or (3) as claimed in claim 2, wherein the silicic acid (hetero)polycondensate and the filler have a refractive index difference $\Delta_{nD}$ the region of ±0.001.

4. Silicic acid (hetero)polycondensate comprising structures of formula (1), (2), or (3), as claimed in claim 1, in the form of bulk materials, composites, cements, adhesives, casting compounds, coating materials, adhesion promoters, fillers, fibers, and priming materials for fillers of fibers.

5. Silicic acid (hetero)polycondensate comprising structures of formula (1), (2), or (3), as claimed in claim 2, in the form of bulk materials, composites, cements, adhesives, casting compounds, coating materials, adhesion promoters, fillers, fibers, and priming materials for fillers of fibers.

6. Compound mixture or silicic acid (hetero)polycondensate according to claim 1, comprising
(i) a compound or structures as specified in formula (1) and a compound or structures of formula (2), or
(ii) a compound or structures as specified in formula (1) and a compound or structures of formula (3), or
(iii) a compound or structures as specified in formula (1), a compound or structure of formula (2) and a compound or structures of formula (3).

7. Compound mixture or silicic acid (hetero)polycondensate according to claim 6, further comprising a particulate filler dispersed therein.

8. Compound mixture or silicic acid (hetero)polycondensate according to claim 7, wherein the silicic acid (hetero)polycondensate and the filler have a refractive index difference $\Delta_{nD}$ in the region of ±0.001.

9. Compound mixture or silicic acid (hetero)polycondensate according to claim 6 in the form of bulk materials, composites, cements, adhesives, casting compounds, coating materials, adhesion promoters, fillers, fibers, and priming materials for fillers of fibers.

10. Compound mixture or silicic acid (hetero)polycondensate according to claim 7 in the form of bulk materials, composites, cements, adhesives, casting compounds, coating materials, adhesion promoters, fillers, fibers, and priming materials for fillers of fibers.

11. Organically cross-linked silicic acid (hetero)polycondensate, comprising structures of formula (2) according to claim 1 in which
(i) some or all of the R¹ residues are cross-linked to each other via polymerization, or
(ii) some or all of the R¹ residues are cross-linked via Michael addition with di- or higher thiols or di- or higher amines, or
(iii) some or all of the R¹ residues are cross-linked to each other via polymerization, and wherein the organically cross-linked silicic acid (hetero)polycondensate further comprises structures of formula (0)

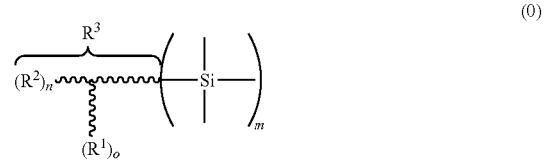

(0)

wherein the residues and substituents R², R³, o and n have the same meaning as in formula (1) and R¹ has the same meaning as in formula (2), with the proviso that some or all of the R¹ residues are cross-linked to each other via polymerization or via Michael addition with di- or higher thiols or di- or higher amines, or with R¹ residues of the structure of formula (2), or
(iv) some or all of the R¹ residues are cross-linked to each other via polymerization, and wherein the organically cross-linked silicic acid (hetero)polycondensate further comprises structures of formula (1), or (v) some or all of the $R^1$ residues are cross-linked via Michael addition with di- or higher thiols or di- or higher amines, and wherein the organically cross-linked silicic acid (hetero)polycondensate further comprises structures of formula (1), or (vi) some or all of the $R^1$ residues are cross-linked to each other via polymerization and some or all of the $R^1$ residues are cross-linked via Michael addition with di- or higher thiols or di- or higher amines, wherein the organically cross-linked silicic acid (hetero)polycondensate further comprises structures of formula (1).

12. Organically cross-linked silicic acid (hetero)polycondensate according to claim 11, further comprising a particulate filler dispersed therein.

13. Organically cross-linked silicic acid (hetero)polycondensate according to claim 12, wherein the silicic acid (hetero)polycondensate and the filler have a refractive index difference $\Delta_{nD}$ in the region of ±0.001.

14. Organically cross-linked silicic acid (hetero)polycondensate according to claim 11 in the form of bulk materials, composites, cements, adhesives, casting compounds, coating materials, adhesion promoters, fillers, fibers, and priming materials for fillers of fibers.

15. Organically cross-linked silicic acid (hetero)polycondensate according to claim 13 in the form of bulk materials, composites, cements, adhesives, casting compounds, coating materials, adhesion promoters, fillers, fibers, and priming materials for fillers of fibers.

16. Method for producing a compound of formula (1) or a silicic acid (hetero)polycondensate comprising structures of formula (1) according to claim 1, comprising the steps:
providing a silane or a silicic acid (hetero)polycondensate with the structure of formula (0),

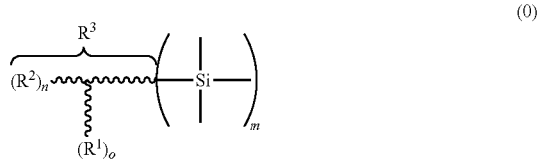

(0)

wherein the residues and substituents $R^1$, $R^2$, $R^3$, m, n and o have the same meaning as in formula (1) and reacting said silane or silicic acid (hetero)polycondensate with a compound of formula (II)

$$X—(Ar)_b \quad (II)$$

wherein the groups, residues and indices Ar and b have the meanings specified for formula (1) and X is selected from HS—, HNR$^4$—, HP(O)R$^4_c$Z'$_d$—, with Z'=OR$^4$ and R$^4$ has the meaning specified for formula (1), c=0 or 1, d=0 or 1 and (c+d)=1, HN= and HP(O)=.

17. Method according to claim 16, where the molar ratio of the $R^1$ groups in the silane or of the structure (0) to compound (II) is between 5:1 and 1:1.

18. Method for producing a compound of formula (2) or a silicic acid (hetero)polycondensate comprising structures of formula (2) according to claim 1, comprising the steps:
providing a silane or a silicic acid (hetero)polycondensate with the structure of formula (1),

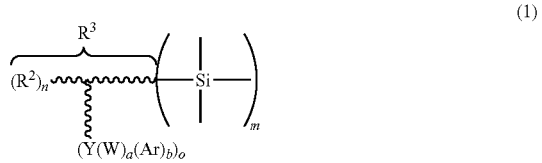

(1)

wherein the groups, residues and indices have the same meaning as specified for structure (1), and reacting said silane or silicic acid (hetero)polycondensate with a compound of formula (III)

$$Q\text{-}W(R^1)_b \quad (III)$$

wherein Q is selected from an isocyanate group, an epoxy group and, with the proviso that $R^2$ in formula (1) is an OH-Group, from a carboxylic acid group —COOH which can be present in activated form and, with the proviso that $R^2$ is a carboxylic acid group or a salt or an ester thereof, from an OH-Group, W is a substituted or unsubstituted hydrocarbon residue, the chain of which can be interrupted by —S—, —O—, —NH—, —NR$^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, $R^1$ is a straight chain or branched, organically polymerizable group, which carries at least one C=C double bond, and b is 1, 2, 3, or an integer greater than 3, where the compound of formula (III) is employed in a stoichiometric or sub- or over-stoichiometric amount relative to the molar amount of $R^2$.

19. Method for producing a compound having formula (3) or a silicic (hetero)polycondensate comprising structures of formula (3) according to claim 1, comprising the steps:
providing a silane or a silicic acid (hetero)polycondensates with the structure of formula (1),

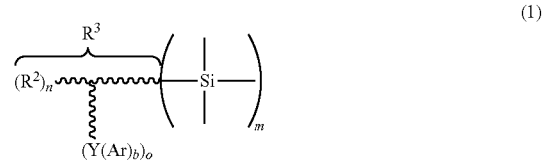

(1)

wherein the groups, residues and indices have the same meaning as specified for structure (1), and reacting said silane or silicic acid (hetero)polycondensate with a compound of formula (IV)

$$Q\text{-}W'\text{[-}Q]_f \quad (IV)$$

wherein Q is selected from an isocyanate group, an epoxy group and, with the proviso that $R^2$ in formula (1) is an OH group, from a carboxylic acid group —COOH or an activated carbonyl compound derived therefrom and, with the proviso that $R^2$ is a carboxylic acid group, from an OH group, or wherein two Q residues together are part of a cyclic, intramolecular anhydride of a dicarboxylic acid (—C(O)O(O)C—), W' is either a substituted or unsubstituted hydrocarbon residue, the chain of which can be interrupted by —S—, —O—, —NH—, —NR$^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, and/or —NHC(S)O— or, with the proviso that each Q is an activated carboxylic acid group and f is equal to 1, represents a single bond, where in the case that Q is part of a cyclic intramolecular anhydride of a dicarboxylic acid, W' is bonded via two carbon atoms with the —C(O)O(O)C— group, and f is 1, 2, 3, 4, 5 or 6 where the compound of formula (IV) is employed in such a stoichiometric ratio that the number of $R^2$ residues and the number of the Q groups are present in a ratio of 1:1, or an excess of Q groups is present.

20. Method for producing a compound mixture or silicic acid (hetero)polycondensate according to claim 6, wherein variant (i) comprises the steps:
providing a silane or a silicic acid (hetero)polycondensate with the structure of formula (1), (1)

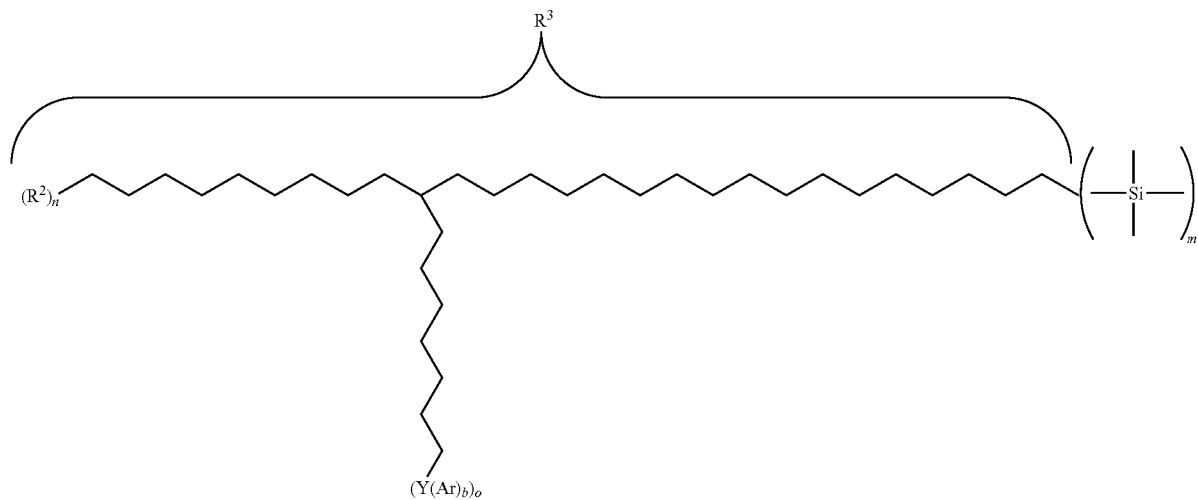

wherein the groups, residues and indices have the same meaning as specified for structure (1), and reacting said silane or silicic acid (hetero)polycondensate with a compound of formula (III)

Q-W(R$^1$)$_b$  (III)

wherein Q is selected from an isocyanate group, an epoxy group and, with the proviso that R$^2$ in formula (1) is an OH group, from a carboxylic acid group —COOH which can be present in activated form and, with the proviso that R$^2$ is a carboxylic acid group or a salt or an ester thereof, from an OH group, W is a substituted or unsubstituted hydrocarbon residue, the chain of which can be interrupted —S—, —O—, —NH—, —NR$^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, R$^1$ represents a straight chain or branched, organically polymerizable group, which carries at least one C═C double bond, and b is 1, 2, 3, or an integer greater than 3, where the compound of formula (III) is used in a substoichiometric amount relative to the molar amount of R$^2$.

21. Method for producing a compound mixture or silicic acid (hetero)polycondensate according to claim 6, wherein variant (ii) comprises the steps:

providing a silane or a silicic acid (hetero)polycondensate with the structure of formula (1), (1)

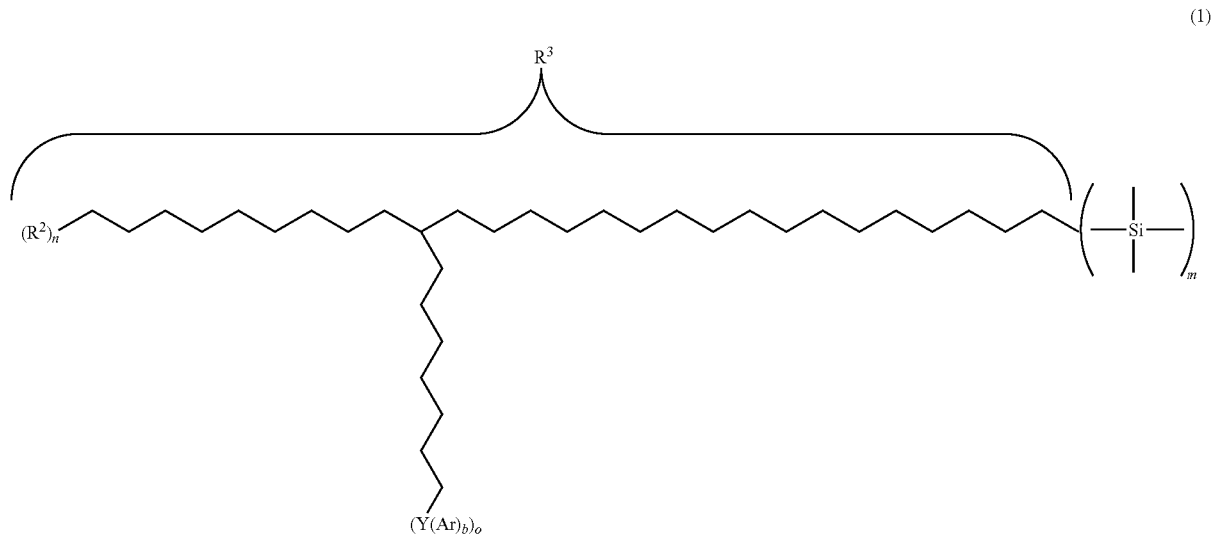

wherein the groups, residues and indices have the same meaning as specified for structure (1), and reacting said silane or silicic acid (hetero)polycondensate with a compound of formula (IV)

wherein Q is selected from an isocyanate group, an epoxy group and, with the proviso that $R^2$ in formula (1) is an OH group, from a carboxylic acid group —COOH or an activated carbonyl compound derived therefrom and, with the proviso that $R^2$ is a carboxylic acid group, from an OH group, or wherein two residues Q together are part of a cyclic, intramolecular anhydride of a dicarboxylic acid (—C(O)O(O)C—), W' is either a substituted or unsubstituted hydrocarbon residue, the chain of which can be interrupted by —S—, —O—, —NH—, —NR$^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, and/or —NHC(S)O— or, with the proviso that each Q is an activated carboxylic acid group and f is equal to 1, represents a single bond, where in the case that Q is part of a cyclic intramolecular anhydride of a dicarboxylic acid, W' is bonded via two carbon atoms with the —C(O)O(O)C— group, and f is 1, 2, 3, 4, 5 or 6 where the compound of formula (IV) in employed in such a stoichiometric ratio that the number of $R^2$ residues are greater than the number of Q groups.

22. Method for producing a compound mixture or silicic acid (hetero)polycondensate according to claim 6, wherein variant (iii) comprises the steps:

providing a silane or a silicic acid (hetero)polycondensate with the structure of formula (1), OH group, from a carboxylic acid group —COOH which can be present in activated form and, with the proviso that $R^2$ is a carboxylic acid group or a salt or an ester thereof, from an OH group, W is a substituted or unsubstituted hydrocarbon residue, the chain of which can be interrupted by —S—, —O—, —NH—, —NR$^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, —NHC(S)O—, $R^1$ is a straight chain or branched, organically polymerizable group, which carries at least one C=C double bond, and b is 1, 2, 3, or an integer greater than 3, in a molar amount of $\alpha$, and reacting said compound mixture or silicic acid (hetero)polycondensate with a compound of formula (IV)

wherein Q is selected from an isocyanate group, an epoxy group and, with the proviso that $R^2$ in formula (1) is an OH group, from a carboxylic acid group —COOH or an activated carbonyl compound derived therefrom and, with the proviso that $R^2$ is a carboxylic acid group, from an OH group, or wherein two residues Q together are part of a cyclic, intramolecular anhydride of a dicarboxylic acid (—C(O)O(O)C—), W' is either a substituted or unsubstituted hydrocarbon residue, the chain of which can be interrupted by —S—, —O—, —NH—, —NR$^4$—, —C(O)O—, —NHC(O)—, —C(O)NH—, —NHC(O)O—, —C(O)NHC(O)—, —NHC(O)NH—, —S(O)—, —C(S)O—, —C(S)NH—, —NHC(S)—, and/or —NHC(S)O—, or, with the proviso that each Q is an activated carboxylic acid group and f is equal to 1, represents a single bond,

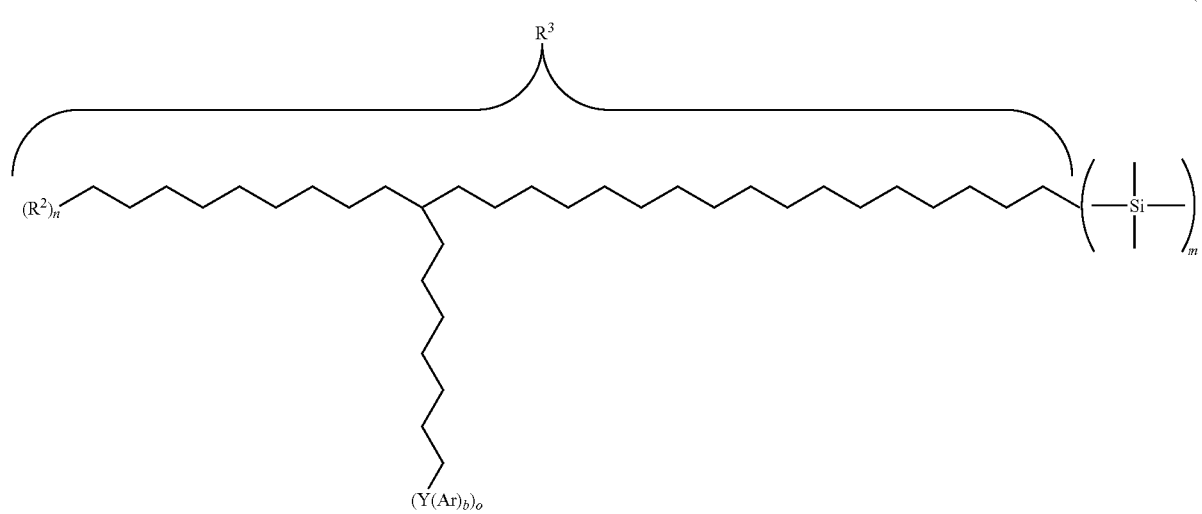

(1)

wherein the groups, residues and indices have the same meaning as specified for structure (1), reacting said compound mixture or silicic acid (hetero)polycondensate with a compound of formula (III)

wherein Q is selected from an isocyanate group, an epoxy group and, with the proviso that $R^2$ in formula (1) is an where in the case that Q is part of a cyclic intramolecular anhydride of a dicarboxylic acid, W' is bonded via two carbon atoms to the —C(O)O(O)C— group, and f is 1, 2, 3, 4, 5 or 6, in a molar amount $\beta/(f+1)$, relative to the index fin formula (IV), where the molar amounts are selected such the condition $\alpha+\beta/(f+1)<n$ is met, where the index n denotes the molar amount of groups $R^2$ in the amount of compounds or silicic acid (hetero)polycondensate of structure (1) used.

\* \* \* \* \*